United States Patent
Ahmed et al.

(10) Patent No.: US 8,217,024 B2
(45) Date of Patent: Jul. 10, 2012

(54) CONJUGATED ESTROGEN COMPOSITIONS, APPLICATORS, KITS, AND METHODS OF MAKING AND USE THEREOF

(75) Inventors: Salah U. Ahmed, New City, NY (US); Madhu Sudhan Shaik, Harriman, NY (US); Sanjeev K. Gupta, Washington Township, NJ (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 981 days.

(21) Appl. No.: 11/645,807

(22) Filed: Dec. 27, 2006

(65) Prior Publication Data

US 2007/0191321 A1    Aug. 16, 2007

Related U.S. Application Data

(60) Provisional application No. 60/753,399, filed on Dec. 27, 2005.

(51) Int. Cl.
*A61K 31/56* (2006.01)

(52) U.S. Cl. ........... 514/170; 514/182

(58) Field of Classification Search ........... 514/182, 514/170
See application file for complete search history.

(56) References Cited

U.S. PATENT DOCUMENTS

| | | |
|---|---|---|
| 2,834,712 A | 5/1958 | Beail et al. |
| 3,608,075 A | 9/1971 | Glen et al. |
| 3,639,599 A | 2/1972 | Mehrhof et al. |
| 4,154,820 A | 5/1979 | Simoons |
| 4,629,449 A | 12/1986 | Wong |
| 4,826,831 A | 5/1989 | Plunkett et al. |
| 5,288,717 A | 2/1994 | Raveendranath et al. |
| 5,340,586 A | 8/1994 | Pike et al. |
| 5,545,635 A | 8/1996 | Bryant et al. |
| 5,719,137 A | 2/1998 | Washburn et al. |
| 5,789,442 A | 8/1998 | Garfield et al. |
| 5,891,868 A | 4/1999 | Cummings et al. |
| 5,897,539 A | 4/1999 | Elliesen et al. |
| 5,898,038 A | 4/1999 | Yallampalli et al. |
| 5,908,638 A | 6/1999 | Huber |
| 5,993,856 A | 11/1999 | Ragavan et al. |
| 6,028,106 A | 2/2000 | Garfield et al. |
| 6,060,077 A | 5/2000 | Meignant |
| 6,103,266 A | 8/2000 | Tapolsky et al. |
| 6,159,959 A | 12/2000 | Miller |
| 6,169,082 B1 | 1/2001 | Raveendranath et al. |

(Continued)

FOREIGN PATENT DOCUMENTS

EP    0147146    7/1985

(Continued)

OTHER PUBLICATIONS

Garg et al., Pharmaceutical Technology, Drug Delivery 2001, pp. 14-24.*

(Continued)

*Primary Examiner* — San-Ming Hui
(74) *Attorney, Agent, or Firm* — Sterne, Kessler, Goldstein & Fox P.L.L.C.

(57) ABSTRACT

The present invention is directed to monophasic pharmaceutical compositions comprising a conjugated estrogen and a hydrophilic or lipophilic excipient. The present invention is also directed to kits and applicators comprising the pharmaceutical compositions. The invention is also directed to methods for treating menopausal conditions in a female comprising administration of the pharmaceutical compositions.

32 Claims, 10 Drawing Sheets

U.S. PATENT DOCUMENTS

| | | | |
|---|---|---|---|
| 6,239,122 B1 | 5/2001 | Steele | |
| 6,416,778 B1 | 7/2002 | Ragavan et al. | |
| 6,455,568 B2 | 9/2002 | Jenkins et al. | |
| 6,458,778 B1 | 10/2002 | Kong et al. | |
| 6,525,039 B1 | 2/2003 | Shah et al. | |
| 6,649,779 B2 | 11/2003 | Kagan et al. | |
| 6,652,874 B2 | 11/2003 | Ragavan et al. | |
| 6,660,726 B2 | 12/2003 | Hill et al. | |
| 6,693,207 B2 | 2/2004 | Kagan et al. | |
| 6,747,019 B2 | 6/2004 | Casper et al. | |
| 6,825,234 B2 | 11/2004 | Yeager et al. | |
| 6,844,334 B2 | 1/2005 | Hill et al. | |
| 6,855,703 B1 | 2/2005 | Hill et al. | |
| 6,977,250 B2 | 12/2005 | Rodriguez | |
| 2001/0031747 A1 | 10/2001 | deZiegler et al. | |
| 2001/0034340 A1 | 10/2001 | Pickar | |
| 2002/0151530 A1 | 10/2002 | Leonard et al. | |
| 2002/0173499 A1 | 11/2002 | Pickar | |
| 2002/0177582 A1 | 11/2002 | Maloney | |
| 2003/0130244 A1 | 7/2003 | Bilkey et al. | |
| 2003/0157157 A1 | 8/2003 | Luo et al. | |
| 2003/0191096 A1 | 10/2003 | Leonard et al. | |
| 2003/0195177 A1 | 10/2003 | Leonard et al. | |
| 2003/0216366 A1 | 11/2003 | Leonard et al. | |
| 2003/0216367 A1 | 11/2003 | Pickar | |
| 2003/0216368 A1 | 11/2003 | Grubb et al. | |
| 2004/0033968 A1 | 2/2004 | Lin et al. | |
| 2004/0044080 A1 | 3/2004 | Place et al. | |
| 2004/0072808 A1 | 4/2004 | Leonard | |
| 2004/0147496 A1 | 7/2004 | Hill et al. | |
| 2004/0192598 A1 | 9/2004 | Kragie | |
| 2004/0198670 A1 | 10/2004 | Hill et al. | |
| 2004/0220152 A1 | 11/2004 | Ben-Maimon et al. | |
| 2004/0259817 A1 | 12/2004 | Waldon et al. | |
| 2004/0259851 A1 | 12/2004 | Leonard | |
| 2005/0143359 A1 | 6/2005 | Bell et al. | |
| 2006/0040904 A1 | 2/2006 | Ahmed et al. | |
| 2006/0142258 A1 | 6/2006 | Pickar | |
| 2006/0154907 A1 | 7/2006 | Leonard et al. | |
| 2008/0021003 A1 | 1/2008 | Hanes et al. | |
| 2008/0051377 A1 | 2/2008 | Ahmed et al. | |
| 2008/0070882 A1 | 3/2008 | Ahmed et al. | |
| 2008/0085877 A1 | 4/2008 | Bortz | |
| 2009/0124584 A1 | 5/2009 | Lyle | |
| 2009/0318510 A1 | 12/2009 | Drizen | |
| 2010/0021529 A1 | 1/2010 | Schafer et al. | |

FOREIGN PATENT DOCUMENTS

| | | | |
|---|---|---|---|
| EP | 0 253 607 B2 | | 1/1988 |
| RU | 2209090 C2 | | 7/2003 |
| WO | WO 95/07701 | | 3/1995 |
| WO | WO01/68074 | * | 9/2001 |
| WO | WO 03/082299 | | 10/2003 |
| WO | WO 2006/023496 A2 | | 3/2006 |
| WO | WO 2006/138715 A1 | | 12/2006 |

OTHER PUBLICATIONS

Remington Pharmaceutical Sciences, 1990, p. 1539-1540.*
First Office Action in U.S. Appl. No. 10/919,529, mailed Jun. 1, 2007.
Reply to First Office Action in U.S. Appl. No. 10/919,529, filed Sep. 4, 2007.
Search Report for PCT Application No. US2006/049328, dated Aug. 8, 2007.
Written Opinion for PCT Application No. US2006/049328, dated Aug. 8, 2007.
Bachmann, G., "Urogenital ageing: an old problem newly recognized," *Maturitas* 22 *Suppl.*:S1-S5, Elsevier Science Ireland Ltd. (1995).
Bachmann, G.A., and Nevadunksy, N.S., "Diagnosis and Treatment of Atrophic Vaginitis," *Am. Fam. Physician 61*:3090-3096, American Academy of Family Physicians (2000).
Beers, M.H., and Berkow, R., eds., "Menopause," in *The Merck Manual of Diagnosis and Therapy*, 17th Edition, Merck Research Laboratories, Whitehouse Station, NJ, pp. 1942-1944 (1999).
Cardozo, L., et al., "Meta-Analysis of Estrogen Therapy in the Management of Urogenital Atrophy in Postmenopausal Women: Second Report of the Hormones and Urogenital Therapy Committee," *Obstet. Gynecol.* 92:722-727, The American College of Obstetricians and Gynecologists (1998).
Carlström, K., et al., "Effects of intravaginal oestrogen treatment upon the vaginal absorption of conjugated equine oestrogens," *Maturitas* 4:277-283, Elsevier Biomedical Press (1982).
Cenestin® Prescribing Information, Revised Jan. 2003, Duramed Pharmaceuticals, Inc., Cincinnati, OH.
Enjuvia® Package Insert, Revised May 4, 2004, Duramed Pharmaceuticals, Inc., Pomona, NY.
Furuhjelm, M., et al., "Intravaginal Administration of Conjugated Estrogens in Premenopausal and Postmenopausal Women," *Int. J. Gynaecol. Obstet.* 17:335-339, Elsevier Ltd. (1980).
Garg, S., et al., "Compendium of Pharmaceutical Excipients for Vaginal Formulations," *Pharma. Technol.*, p. 14-24, Advanstar Communications, Inc. (2001).
Greendale, G.A., and Judd, H.L., "The Menopause: Health Implications and Clinical Management," *J. Am. Geriatr. Soc.* 41:426-436, Williams & Wilkins (1993).
Gupta, P., and Garg, S., "Recent Advances in Semisolid Dosage Forms for Dermatological Application," *Pharma. Technol.*, p. 144-162, Advanstar Communications, Inc. (2002).
Hilton, P., and Stanton, S.L., "The use of intravaginal oestrogen cream in genuine stress incontinence," *Br. J. Obstet. Gynaecol.* 90:940-944, Blackwell Scientific Publications (1983).
Hulley, S.B., and Grady, D., "The WHI Estrogen-Alone Trial—Do Things Look Any Better?" *J. Am. Med. Assoc.* 291:1769-1771, American Medical Association (Apr. 2004).
Luisi, M., et al., "A Group-Comparative Study of Effects of Ovestin Cream Versus Premarin Cream in Post-Menopausal Women with Vaginal Atrophy," *Maturitas* 2:311-319, Elsevier/North-Holland Biomedical Press (1980).
Mandel, F.P., et al., "Biological Effects of Various Doses of Vaginally Administered Conjugated Equine Estrogens in Postmenopausal Women," *J. Clin. Endocrinol. Metab.* 57:133-139, The Endocrine Society (1983).
Manonai, J., et al., "The Effect of Estradiol Vaginal Tablet and Conjugated Estrogen Cream on Urogenital Symptoms in Postmenopausal Women: A Comparative Study," *J. Obstet. Gynaecol. Res.* 27:255-260, University of Tokyo Press (2001).
Martin, P.L., "Systemic Absorption and Sustained Effects of Vaginal Estrogen Creams," *J. Am. Med. Assoc.* 242:2699-2700, American Medical Association (1979).
Marx, P., et al., "Low-dose (0.3 mg) synthetic conjugated estrogens A is effective for managing atrophic vaginitis," *Maturitas* 47:47-54, Elsevier Ireland Ltd. (Jan. 2004).
Metrogel-Vaginal®, *Physician's Desk Reference, 56th Edition*, p. 1986, Medical Economics Company, Inc., Montvale, NJ (2002).
Nelson, H.D., "Commonly Used Types of Postmenopausal Estrogen for Treatment of Hot Flashes," *J. Am. Med. Assoc.* 291:1610-1620, American Medical Association (Apr. 2004).
Nilsson, K., et al., "The vaginal epithelium in the postmenopause—cytology, histology and pH as methods of assessment," *Maturitas* 21:51-56, Elsevier Science Ireland Ltd. (1995).
Pandit, L., and Ouslander, J.G., "Postmenopausal Vaginal Atrophy and Atrophic Vaginitis," *Am. J. Med. Sci.* 314:228-231, Lippincott-Raven Publishers (1997).
Premarin® Vaginal Cream, Prescribing Information and Information for the Patient, Revised Sep. 11, 2001, Ayerst Laboratories, Philadelphia, PA.
Rigg, L.A., et al., "Absorption of Estrogens from Vaginal Creams," *N. Engl. J. Med.* 298:195-197, Massachusetts Medical Society (1978).
Semmens, J.P., and Wagner, G., "Estrogen Deprivation and Vaginal Function in Postmenopausal Women," *J. Am. Med. Assoc.* 248:445-448, American Medical Association (1982).
Stevens, R.E., et al., "A 12-Week Clinical Trial Determining the Efficacy of Synthetic Conjugated Estrogens, A (SCE), in the Treatment of Vasomotor Symptoms in Menopausal Women," *Int. J. Fertil.* 45:264-272, MSP International, Inc. (2000).
Stevens, R.E., et al., "Evaluation of Single- and Multiple-Dose Pharmacokinetics of Synthetic Conjugated Estrogens, A (Cenestin®) Tablets: A Slow-Release Estrogen Replacement Product," *J. Clin. Pharmacol.* 42:332-341, American College of Clinical Pharmacology (2002).

Utian, W.H., et al., "Relief of Hot Flushes With New Plant-Derived 10-Component Synthetic Conjugated Estrogens," *Obstet. Gynecol.* 103:245-253, The American College of Obstetricians and Gynecologists (Feb. 2004).

Willhite, L.A., and O'Connell, M.B., "Urogenital Atrophy: Prevention and Treatment," *Pharmacotherapy* 21:464-480, Pharmacotherapy Publications, Inc. (2001).

Zhao, L., et al., "An Estrogen Replacement Therapy Containing Nine Synthetic Plant-Based Conjugated Estrogens Promotes Neuronal Survival," *Exp. Biol. Med.* 228:823-835, Society for Experimental Biology and Medicine (Jul. 2003).

Dickerson, J., et al., "Efficacy of estradiol vaginal cream in postmenopausal women," *Clin. Pharmacol. Ther.* 26:502-507, Mosby (1979).

Dickey, R.P., et al., "Oral Contraception: Realizing the Promise by Overcoming the Pitfalls," in *Individualizing Oral Contraceptive Therapy: A Supplement to OBG Management*, Dowden Publishing, Montvale, NJ, pp. 2-6 (2000).

Estrace® Cream, Prescribing Information and Information for the Patient, Bristol-Myers Squibb Company, Princeton, NJ, 2 pages (Revised Jun. 2003).

Estring®, Information for Patients, Pharmacia Corp., Kalamazoo, MI, 24 pages (Revised 2002).

Estring®, Physician's Leaflet, Pharmacia Corp., Kalamazoo, MI, 28 pages (Revised 2002).

Kuhl, H., "Comparative Pharmacology of Newer Progestogens," *Drugs* 51:188-215, ADIS Press (1996).

Lundeen, S.G., et al., "Rat uterine complement C3 expression as a model for progesterone receptor modulators: characterization of the new progestin trimegestone," *J. Steroid Biochem. Molec. Biol.* 78:137-143, Pergamon Press (2001).

Osmers, R., et al., "Vaginosonography for early detection of endometrial carcinoma," *Lancet* 335:1569-1571, Lancet Publishing Group (1990).

Philibert, D., et al., "The pharmacological profile of a novel norpregnane progestin (trimegestone)," *Gynecol. Endocrinol.* 13:316-326, Parthenon Publishing (1999).

Rigg, L., "Estrogen Replacement Therapy for Atrophic Vaginitis," *Int. J. Fertil.* 31:29-34, MSP International (1986).

Rosen, R., et al., "Prevalence of Sexual Dysfunction in Women: Results of a Survey Study of 329 Women in an Outpatient Gynecological Clinic," *J. Sex Marital Ther.* 19:171-188, Behavioral Publications (1993).

Udoff, L., et al., "Combined Continuous Hormone Replacement Therapy: A Critical Review," *Obstet. Gynecol.* 86:306-316, The American College of Obstetricians and Gynecologists (1995).

Vagifem®, Information for Patients, Novo Nordisk Pharmaceuticals, Inc., Princeton, NJ, 2 pages (Revised Jul. 2003).

International Search Report for International Application No. PCT/US05/29123, United States Patent and Trademark Office, Alexandria, VA, mailed on Dec. 22, 2006.

Office Action dated Jan. 11, 2008, in U.S. Appl. No. 10/919,529, Ahmed, S. et al., filed Aug. 17, 2004.

Office Action dated Feb. 6, 2009, in U.S. Appl. No. 10/919,529, Ahmed, S. et al., filed Aug. 17, 2004.

Office Action dated Nov. 12, 2009, in U.S. Appl. No. 10/919,529, Ahmed, S. et al., filed Aug. 17, 2004.

Office Action dated Mar. 18, 2010, in the U.S. Appl. No. 11/889,976, Ahmed, S. et al., filed Aug. 17, 2007.

*Duramed Pharmaceuticals, Inc. v. Paddock Laboratories, Inc.*, Civil Docket Case #:09-CV-1905, U.S. District Court, Southern District of New York (Foley Square), filed on Mar. 2, 2009, 6 pages.

*Duramed Pharmaceuticals, Inc. v. Paddock Laboratories, Inc.*, Civil Docket Case #:09-CV-1905 (LBS) (AJP), U.S. District Court, Southern District of New York (Foley Square), "*Defendant Paddock Laboratories, Inc.'s Answer and Defenses to Plaintiff's Complaint*," Filed on Mar. 23, 2009, 8 pages.

*Duramed Pharmaceuticals, Inc. v. Paddock Laboratories, Inc.*, Civil Docket Case #: 09-CV-1905 (LBS) (AJP), U.S. District Court, Southern District of New York (Foley Square), "*Defendant Paddock Laboratories, Inc.'s Answer and Defenses to Plaintiff's Complaint*," Filed on May 7, 2009, 9 pages.

English language translation of the Office Action for Russian Patent No. 2008130890, received on Sep. 14, 2010, Patent Office of the Russian Federation, Russia, 4 pages.

English language (unverified) translation of abstract of Russian Patent No. 2209090 C2, Zhan-Ljuk, et al., espacenet Database, 1 page (2003).

Goronovskiy, T., et al., "Naukova dumka," in *Abridged Reference Book on Chemistry* (in Russian), pp. 738-739 and 821, Kiev, Ukraine (1984).

"Applicator," entry in the *Encyclopedia of Medical Terms*, pp. 57 (in Russian) (2001).

Ledina, A., "Conjugated estrogens in the treatment of climacteric disorders," in *Gynaecology, Consillium Medium*, vol. 4, No. 6 (Online, in Russian), accessed at: http://www.consilium-medicum.com/magazines/special/gynaecology/article/7516, accessed on Jul. 7, 2010.

Shoupe, D., "HRT dosing regimens: continuous versus cyclic-pros and cons," *Int. J. Fertil. Womens Med.* 46:7-15, Medical Science Pub. International, United States (2001).

Shulman, L., "17β-estradiol/levonorgestrel transdermal system for the management of the symptomatic menopausal woman," *Expert Opin. Pharmacother.* 5:2559-2566, Informa Healthcare, United Kingdom (2004).

\* cited by examiner

CONJUGATED ESTROGEN COMPOSITIONS, APPLICATORS, KITS, AND METHODS OF MAKING AND USE THEREOF

CROSS-REFERENCE TO RELATED APPLICATION

This application claims the benefit of the filing date of U.S. application Ser. No. 60/753,399, filed Dec. 27, 2005, which is hereby incorporated by reference in its entirety.

BACKGROUND OF THE INVENTION

1. Field of the Invention

The present invention is directed to monophasic pharmaceutical compositions comprising a conjugated estrogen and a hydrophilic or lipophilic excipient. The present invention is also directed to kits and applicators comprising the pharmaceutical compositions. The invention is also directed to methods for treating menopausal conditions in a female comprising administering the pharmaceutical compositions.

2. Background of the Invention

Decreased circulating estradiol levels occur with senescence of the ovaries and reduced follicular development, and cause characteristic symptoms at menopause (Bachmann, G. A. and Nevadunsky, N. S., *Am. Fam. Phys.* 61:3090-3096 (2000); Beers, M. R. and Berkow, R., eds., "Gynecology and Abstetrics," in *The Merck Manual of Diagnosis and Therapy,* 17th Edition, Merck Research Laboratories, Whitehouse Station, N.J., 1942-1944 (1999)). Common symptoms include hot flashes, menstrual irregularities, night sweats, chills, insomnia, paresthesias, palpitations, tachycardia, cold hands and feet, headache, anxiety, dizziness, nervousness, depression, irritability, impaired cognition, diminished libido, fatigue, gastrointestinal symptoms, and atrophic vaginitis (Bachmann, G. A. and Nevadunsky, N. S., *Am. Fam. Phys.* 61:3090-3096 (2000); Beers, M. R. and Berkow, R., eds., "Gynecology and Abstetrics," in *The Merck Manual of Diagnosis and Therapy,* 17th Edition, Merck Research Laboratories, Whitehouse Station, N.J., 1942-1944 (1999); Semmens, J. P. and Wagner, G., *J. Am. Med. Assoc.* 248:445-448 (1982); Bachmann, G. A., *Maturitas* 22 (Suppl.):S1-S5 (1995); Greendale, G. A., and Judd, H. L., *J. Am. Geriatr. Soc.* 41:426-436 (1993); Nilsson, K., et al., *Maturitas* 21:51-56 (1995)). Symptoms are frequently severe enough to cause women to seek treatment and may persist for several years during peri-menopause and/or post-menopause.

Estrogen deprivation causes profound changes in the genitourinary tract, and up to 40% of postmenopausal women have symptoms associated with these changes (Greendale, G. A., and Judd, H. L., *J. Am. Geriatr. Soc.* 41:426-436 (1993)). A lack of vaginal lubrication and frequent vaginal infections are experienced by over 50% of post-menopausal women (Rosen, R., et al., *J. Sex & Marital Therapy* 19:171-188 (1993); Bachmann, G. A., *Maturitas* 22 (Suppl.):S1-S5 (1995)). The vaginal mucosa and vulvar skin become thinner, the labia flatten and shrink, and the clitoris, uterus, and ovaries decrease in size (Beers, M. R. and Berkow, R., eds., "Gynecology and Abstetrics," in *The Merck Manual of Diagnosis and Therapy,* 17th Edition, Merck Research Laboratories, Whitehouse Station, N.J. (1999), pp. 1942-1944). Vaginal pH increases from the normal 3.5-4.0 (which favors lactobacilli) to 6.0-8.0 (which favors pathogenic organisms) (Pandit, L., and Ouslander, J. G., *Am. J Med. Sci.* 314:228-231 (1997); Semmens, J. P. and Wagner, G., *J. Am. Med. Assoc.* 248:445-448 (1982)). Decreased pelvic muscle tone leads to urinary frequency, urgency, and incontinence (Bachmann, G. A., *Maturitas* 22 (Suppl.):S1-S5 (1995)). Endocervical glandular tissue becomes less active and mucus secretion decreases (Bachmann, G. A., *Maturitas* 22 (Suppl.):S1-S5 (1995)). The vaginal-epithelium becomes dry and atrophic, which causes inflammation, discomfort, itching, and dyspareunia. The vagina becomes less distensible and elastic and is easily traumatized (Bachmann, G. A. and Nevadunsky, N. S., *Am. Fam. Phys.* 61:3090-3096 (2000)). Cytologic examination of vaginal mucosa shows an increased proportion of parabasal cells and a decreased proportion of superficial cells; e.g., a calculated Maturation Index score<55 (Pandit, L., and Ouslander, J. G., *Am. J. Med. Sci.* 314:228-231 (1997); Bachmann, G. A. and Nevadunsky, N. S., *Am. Fam. Phys.* 61:3090-3096 (2000); Nilsson, K., et al., *Maturitas* 21:51-56 (1995)). Vaginal ultrasonography of the uterine lining will typically demonstrate endometrium thinning to $\leq 5$ mm, signifying decreased estrogen stimulation (Osmers, R., et al., *Lancet* 335:1569-1571 (1990)).

Estrogen therapy (ET) or hormone therapy (HT), if not contraindicated, is the treatment of choice for postmenopausal women with urogenital atrophy (Willhite, L. A. and O'Connell, M. B., *Pharmacotherapy* 21:464-480 (2001); Rigg., L. A., *Int. J. Fertil.* 31:29-34 (1986)). Various forms of HT have been shown to effectively manage menopausal signs and symptoms, including those associated with vaginal atrophy (Cardozo, I., et al., *Obstet. Gynocol.* 92:722-727 (1988); Beers, M. R. and Berkow, R., eds., "Gynecology and Abstetrics," in *The Merck Manual of Diagnosis and Therapy,* 17th Edition, Merck Research Laboratories, Whitehouse Station, N.J., 1942-1944 (1999); Greendale, G. A., and Judd, H. L., *J. Am. Geriatr. Soc.* 41:426-436 (1993); Semmens, J. P. and Wagner, G., *J. Am. Med. Assoc.* 248:445-448 (1982); Bachmann, G. A., *Maturitas* 22 (Suppl.):S1-S5 (1995); Bachmann, G. A. and Nevadunsky, N. S., *Am. Fam. Phys.* 61:3090-3096 (2000); Nilsson, K., et al., *Maturitas* 21:51-56 (1995); Osmers, R., et al., *Lancet* 335:1569-1571 (1990); Rigg., L. A., *Int. J. Fertil.* 31:29-34 (1986); Marx, P., et al., *Maturitas* 47:47-54 (2004)). Estrogen therapy decreases vaginal pH (Bachmann, G. A. and Nevadunsky, N. S., *Am. Fam. Phys.* 61:3090-3096 (2000)), thickens and revascularizes the vaginal epithelium (Bachmann, G. A. and Nevadunsky, N. S., *Am. Fam. Phys.* 61:3090-3096 (2000)), increases the number of superficial cells (thereby increasing the Maturation Index) (Pandit, L., and Ouslander, J. G., *Am. J. Med. Sci.* 314:228-231 (1997)), and rapidly reverses vaginal atrophy (Bachmann, G. A. and Nevadunsky, N. S., *Am. Fam. Phys.* 61:3090-3096 (2000)).

A number of therapeutic regimens for estrogen replacement therapy are known, although many of these regimens comprise oral or transdermal administration of estrogens. For example, administration of conjugated equine estrogens, estradiol, and estriol vaginal creams has been shown to restore vaginal cytology to a premenopausal state and to improve urogenital atrophy (Willhite, L. A. and O'Connell, M. B., *Pharmacotherapy* 21:464-480 (2001)). The cyclic administration of conjugated estrogens daily for three weeks followed by one week off has been proposed (PREMARIN® Vaginal Cream package insert, revised Apr. 28, 2004, Wyeth Pharmaceuticals, Inc., Philadelphia, Pa.). However, results of the Women's Health Initiative (WHI) Study led to FDA recommendations that women receiving estrogen therapy be exposed to the lowest effective dose for the shortest duration of treatment (Hulley and Grady, *J. Am. Med. Assoc.* 291:1769-71 (2004)). Thus, the use of a less frequent dosing regimen for locally administered estrogen replacement therapy has particular appeal.

BRIEF SUMMARY OF THE INVENTION

The present invention is directed to an applicator comprising a single unit-dose of a monophasic pharmaceutical composition comprising a conjugated estrogen and a hydrophilic or lipophilic excipient, wherein the composition has a viscosity greater than about 1 Poise and less than about 30,000 Poise.

In some embodiments, the conjugated estrogen comprises two or more conjugated estrogens.

In some embodiments, the conjugated estrogen comprises sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, or a combination thereof.

In some embodiments, the conjugated estrogen comprises sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, sodium Δ8,9-dehydroestrone sulfate, or a combination thereof.

In some embodiments, the conjugated estrogen consists of a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, and sodium 17β-dihydroequilenin sulfate.

In some embodiments, the conjugated estrogen consists of a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate.

In some embodiments, the composition comprises a hydrophilic phase. In further embodiments, the composition comprises a pharmaceutically acceptable hydrophilic excipient selected from the group consisting of water, glycerin, propylene glycol, polyethylene glycol, polyol, alcohol, and combinations thereof.

In some embodiments, the composition comprises a lipophilic phase. In further embodiments, the composition comprises a pharmaceutically acceptable lipophilic excipient selected from the group consisting of glyceryl esters of fatty acids, monoglycerides, diglycerides, triglycerides, and combinations thereof. In some embodiments, the composition comprises a glyceryl esters of fatty acids with carbon chain lengths of 4 to 24, and combinations thereof. In some embodiments, the composition comprises a pharmaceutically acceptable lipophilic excipient selected from the group consisting of lauric acid, palmitic acid, oleic acid, linoleic acid, linolenic acid, stearic acid, myristic acid, and combinations thereof.

In some embodiments, the composition comprises a pharmaceutically acceptable excipient selected from the group consisting of an alkaline agent, a stabilizer, an adhesion agent, a solvent, a surfactant, a humectant, a buffering agent, and combinations thereof.

In some embodiments, the composition comprises a pharmaceutically acceptable excipient, wherein the excipient is an alkaline agent. The alkaline agent can be an inorganic base selected from the group consisting of hydroxides and oxides of alkali metals, alkaline earth metals, and combinations thereof. The alkaline agent can be an organic base comprising an amine.

In some embodiments, the composition comprises a pharmaceutically acceptable excipient, wherein the excipient is a stabilizer. The stabilizer can be selected from the group consisting of methyl paraben, propyl paraben, t-butyl hydroquinone, butylated hydroxyanisole, butylated hydroxytoluene, ascorbic acid and its esters, vitamin E and its esters, sodium bisulfite, sodium metabisulfite, 3-dehydroshikimic acid, tocopherols and their esters, alkyl gallates, chelating agents, EDTA, edetate disodium, citric acid, benzyl alcohol, and combinations thereof.

In some embodiments, the composition comprises a pharmaceutically acceptable excipient, wherein the excipient is an adhesion agent. The adhesion agent can be selected from the group consisting of hydrogenated vegetable oil, polyethylene glycol, cetyl alcohol, cetyl esters wax, microcrystalline wax, paraffin, ethyl alcohol, stearyl alcohol, lauryl alcohol, myristal alcohol, cetostearyl alcohol, white wax, yellow wax, beeswax, candelilla wax, cotton wax, carnauba wax, bayberry wax, rice-bran wax, carbomer, hydroxypropylmethylcellulose, hypromellose, starch, methylcellulose, microcrystalline cellulose, and combinations thereof.

In some embodiments, the composition comprises a pharmaceutically acceptable excipient, wherein the excipient is a solvent. The solvent can be selected from the group consisting of water, glycerin, dehydrated alcohol, glyceryl esters of fatty acids, lauryl macrogolglycerides, polyoxyethylene alkyl ethers, and combinations thereof.

In some embodiments, the composition comprises a pharmaceutically acceptable excipient, wherein the excipient is a surfactant. The surfactant can be selected from the group consisting of sodium lauryl sulfate, polysorbate 80, poloxamer, lauryl macrogolglycerides, polyoxyethylene alkyl ethers, and combinations thereof.

In some embodiments, the composition comprises a pharmaceutically acceptable excipient, wherein the excipient is a humectant. The humectant can be selected from the group consisting of polyethylene glycol, propylene glycol, glycerin, polyol, polyol derivatives, and combinations thereof.

In some embodiments, the composition comprises a pharmaceutically acceptable excipient, wherein the excipient is a buffering agent. The buffering agent can be selected from the group consisting of Tris buffers, Tris EDTA, Tris acetate, Tris phosphate, Tris glycine, phosphate buffers, sodium phosphate, sodium phosphate dibasic, potassium phosphate, bicarbonate buffers, acetate buffers, ammonium buffers, citrate buffers, organic acid buffers, zwitterionic buffers, and derivatives and combinations thereof.

In some embodiments, the composition is substantially free of ethanol.

In some embodiments, the composition comprises conjugated estrogen in a single unit-dose, wherein the conjugated estrogen is an amount of about 0.1 mg to about 10 mg. In some embodiments, the composition is a single unit-dose in an amount of about 100 mg to about 5 g. In some embodiments, the composition comprises conjugated estrogen in a single unit-dose, wherein the conjugated estrogen is an amount of about 0.1 mg to about 10 mg, wherein the total composition is an amount of about 100 mg to about 5 g.

In some embodiments, the composition comprises conjugated estrogen in a concentrated single unit-dosage form, wherein the conjugated estrogen is in an amount of about 0.02% to about 5% of the total weight of the composition.

In some embodiments, the composition comprises conjugated estrogen in a concentrated single unit-dosage form, wherein the conjugated estrogen is an amount of about 1 mg to about 10 mg of the total composition. In some embodiments, the composition is a single unit-dose in an amount of about 100 mg to about 2 g. In some embodiments, the composition comprises conjugated estrogen in a concentrated single unit-dosage form, wherein the conjugated estrogen is an amount of about 1 mg to about 10 mg of the total composition, wherein the total composition is an amount of about 100 mg to about 2 g.

The present invention is further directed to a monophasic pharmaceutical composition comprising a conjugated estrogen and a lipophilic or hydrophilic excipient, wherein the composition has a viscosity greater than about 1 Poise and less than about 30,000 Poise, and wherein the composition is capable of a percent area of spread up to about 90% over the estimated human vaginal surface area.

The present invention is further directed to a monophasic pharmaceutical composition comprising a conjugated estrogen and a lipophilic or hydrophilic excipient, wherein the composition has a viscosity greater than about 1 Poise and less than about 30,000 Poise, and wherein the diffusion of estrone or equilin from the composition across a cellulose acetate membrane is from about 60% to about 90% at 6 hours.

The present invention is further directed to a monophasic pharmaceutical composition comprising a conjugated estrogen and a lipophilic or hydrophilic excipient, wherein the composition has a viscosity greater than about 1 Poise and less than about 30,000 Poise, and wherein the diffusion of estrone or equilin from the composition across human vaginal tissue is from about 30% to about 90% at 24 hours.

The present invention is further directed to a kit comprising one or more applicators, wherein each applicator comprises a single unit-dose of a monophasic pharmaceutical composition comprising a conjugated estrogen and a lipophilic or hydrophilic excipient, wherein the composition has a viscosity greater than about 1 Poise and less than about 30,000 Poise.

In some embodiments, the kit comprises a vaginal applicator.

In some embodiments, the kit comprises an oral applicator.

In some embodiments, the kit further comprises printed instructions for use of the kit.

The present invention is further directed to a vaginal applicator comprising a single unit-dose of a monophasic pharmaceutical composition comprising a conjugated estrogen and a lipophilic or hydrophilic excipient, wherein the composition has a viscosity greater than about 1 Poise and less than about 30,000 Poise.

The present invention is further directed to an oral applicator comprising a single unit-dose of a monophasic pharmaceutical composition comprising and a lipophilic or hydrophilic excipient, wherein the composition has a viscosity greater than about 1 Poise and less than about 30,000 Poise. In further embodiments, the oral applicator applies the composition as a spray.

The present invention is further directed to a method of treating a menopausal condition in a female in need thereof, the method comprising administering to the female a single unit-dose of a monophasic pharmaceutical composition comprising a conjugated estrogen and a lipophilic or hydrophilic excipient, wherein the composition has a viscosity greater than about 1 Poise and less than about 30,000 Poise.

In some embodiments, the method further comprises transmucosal administration.

In some embodiments, the composition is administered at least once daily for at least 2 consecutive days.

In some embodiments, the composition is administered at least once daily for at least 7 consecutive days.

In some embodiments, the composition is administered at least twice per week for at least 1 week.

In some embodiments, the composition is administered at least twice per week for at least 2 weeks.

In some embodiments, the composition is administered (a) at least once daily for at least 7 consecutive days, then (b) at least twice per week for at least 2 weeks.

In some embodiments, the composition is administered (a) at least once daily for 2 to 13 consecutive days, then (b) at least twice per week for at least 2 weeks.

In some embodiments, the menopausal condition is selected from the group consisting of vaginal dryness, pain during intercourse, increased risk of infections, inability to control urination (incontinence), increased frequency of urinary infections, vaginal atrophy, kraurosis vulvae, hot flashes and night sweats, fatigue, emotional changes (mood swings and changes in sexual interest), sleep disturbances (insomnia), drier skin and hair, increased growth of facial and body hair, aches and pains in the joints, headaches, palpitations (rapid, irregular heart beats), vaginal itching, osteoporosis, and generalized itching.

In some embodiments, the method provides systemic treatment of the menopausal condition.

The present invention is further directed to a method of delivering to a female in need thereof an applicator comprising a single-unit dose of a monophasic pharmaceutical composition comprising a conjugated estrogen and a lipophilic or hydrophilic excipient, wherein the composition has a viscosity greater than about 1 Poise and less than about 30,000 Poise, the method comprising: (a) registering in a computer readable storage medium identity of a physician permitted to prescribe the applicator; (b) providing the female with counseling information concerning a risk attendant to the applicator; (c) obtaining informed consent of the female to receive the composition despite the risk; (d) registering the female in the computer readable medium after obtaining the informed consent; and (e) permitting the female access to the applicator.

BRIEF DESCRIPTION OF THE DRAWINGS/FIGURES

Figure 6:
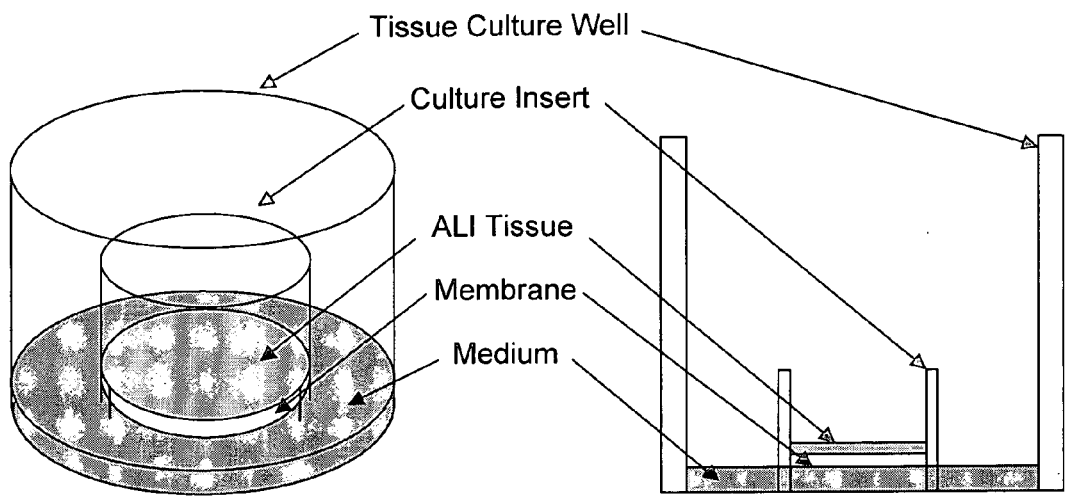
Figure 6:
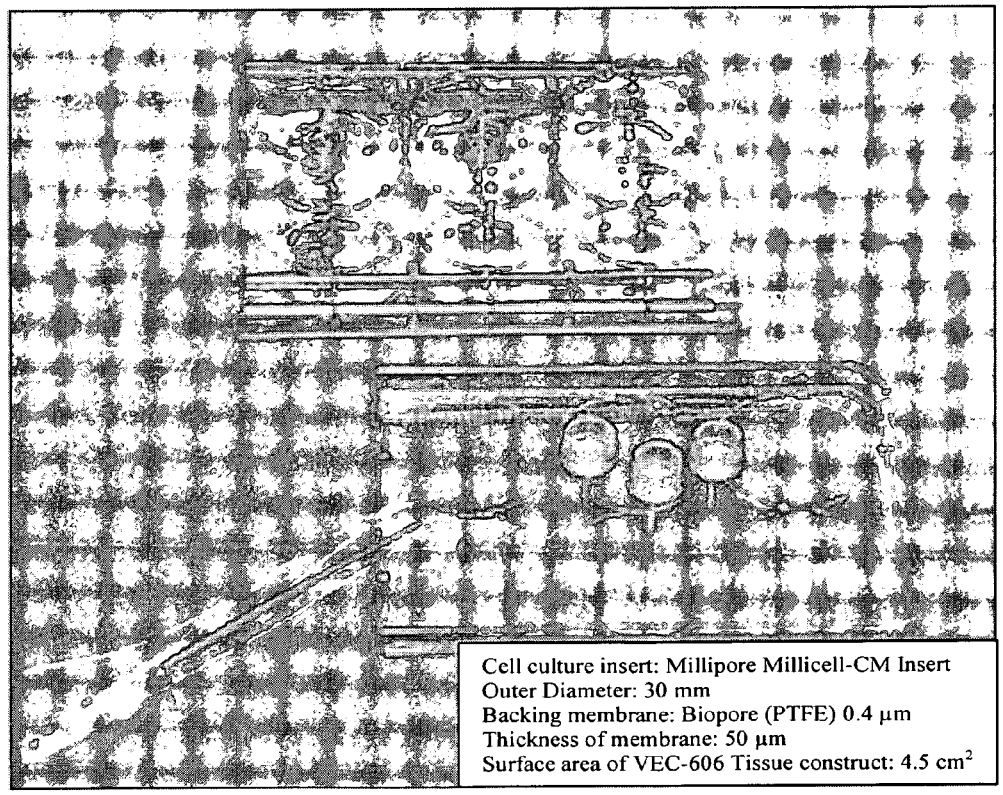

FIG. 6 provides a diagram of a methodology for measuring the in vitro diffusion of conjugated estrogens formulations across normal human vaginal ectocervical tissue.

Figure 7:
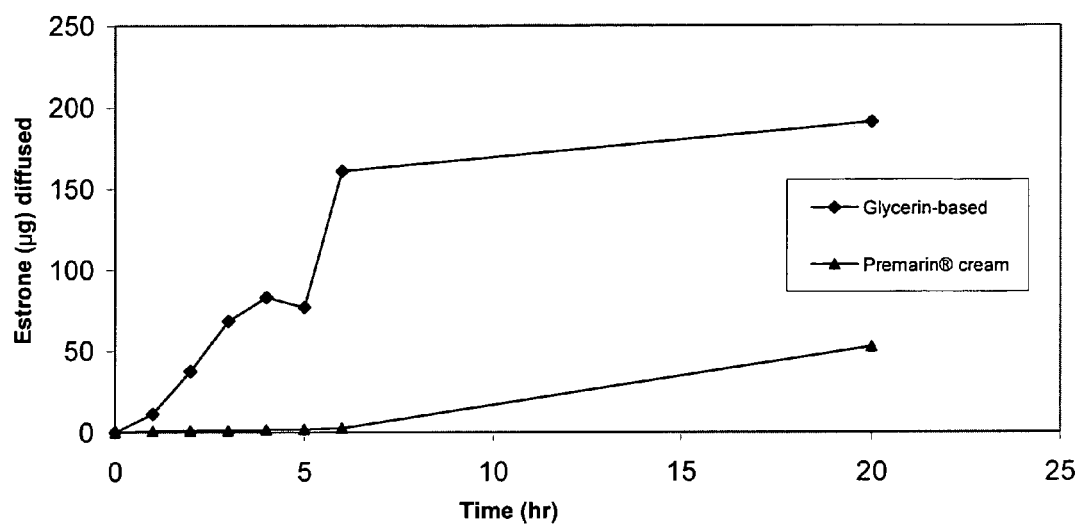

FIG. 7 shows the in vitro diffusion of estrone against normal human vaginal ectocervical tissue of a glycerin-based (♦) formulation containing Conjugated Estrogens (37.5 mg/g) as compared with Premarin® cream (▲).

Figure 8:
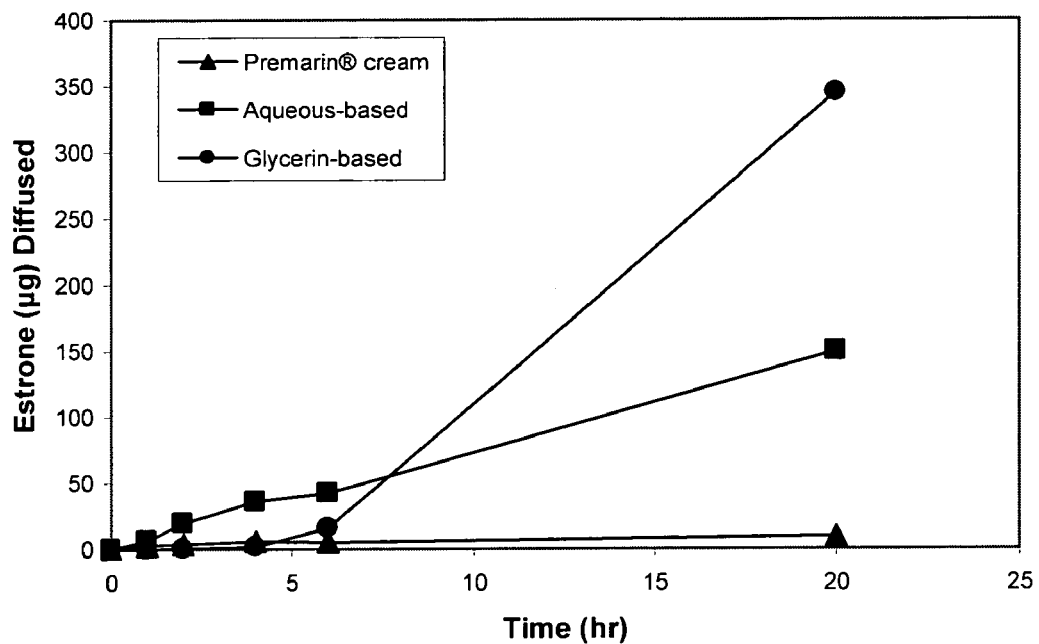

FIG. 8 shows the in vitro diffusion of estrone against normal human vaginal ectocervical tissue of aqueous-based (■) and glycerin-based (●) formulations containing Conjugated Estrogens, USP (Type DE, 525 mg/g) as compared with Premarin® cream (▲).

Figure 9:
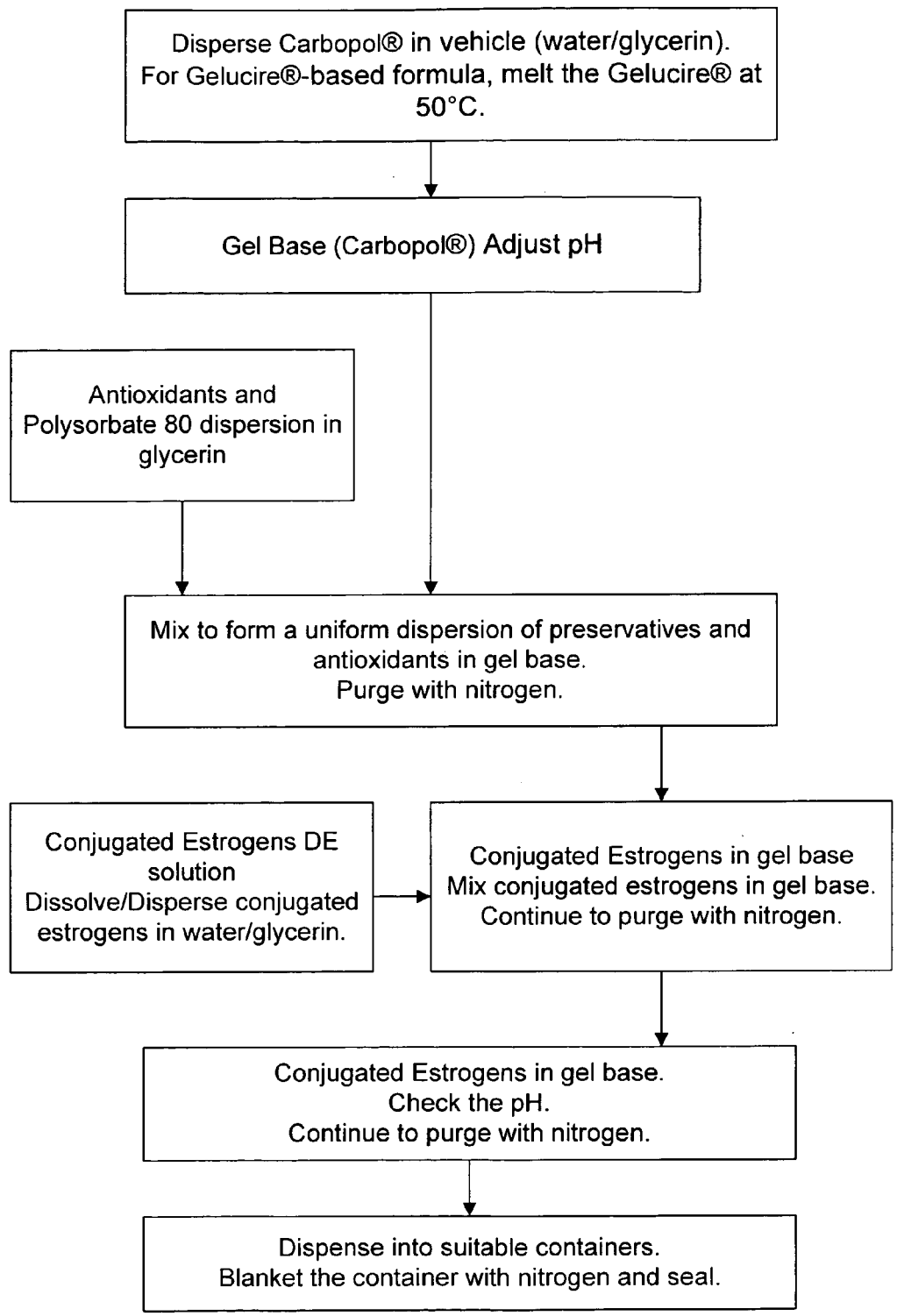

FIG. 9 provides a manufacturing process flow chart for conjugated estrogens aqueous-based, glycerin-based, and Gelucire®-based formulations prepared from Conjugated Estrogens, USP (Type DE, 525 mg/g).

Figure 10:
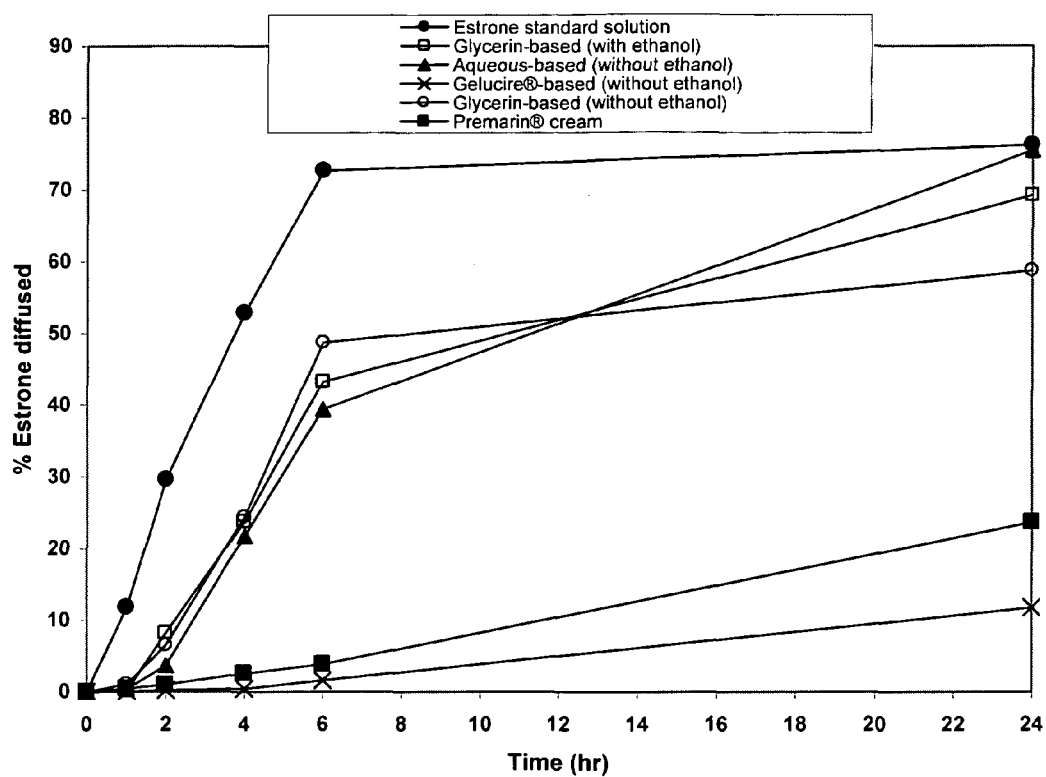

FIG. 10 shows the in vitro diffusion of estrone against normal human vaginal ectocervical tissue of aqueous-based (▲), glycerin-based (○), and Gelucire®-based (X) ethanol-free formulations prepared from Conjugated Estrogens, USP (Type DE, 525 mg/g) as compared with a glycerin-based (□) ethanol-containing formulation prepared from Conjugated Estrogens, USP (Type DE, 525 mg/g), an estrone standard solution (●), and Premarin® cream (■).

DETAILED DESCRIPTION OF THE INVENTION

Pharmaceutical Compositions

The present invention is directed to applicators, monophasic pharmaceutical compositions, and kits comprising a conjugated estrogen and a hydrophilic or lipophilic excipient, and methods for using the same. The embodiments and definitions described are intended to illustrate the invention and are not intended to limit the scope of the invention. In some embodiments, the present invention is directed to monophasic pharmaceutical compositions comprising two or more conjugated estrogens and a lipophilic or hydrophilic excipient. In some embodiments, at least a fraction of at least one conjugated estrogen is present in the composition in a molecular dispersion.

"Monophasic" compositions as described herein are compositions derived from a single liquid phase. One of skill in the art will readily understand that a composition can be derived from a liquid phase, with movement of the liquid phase restricted by components that increase the viscosity or rigidity of the composition. In some embodiments, the single liquid phase comprises one or more liquids that are lipophilic. In some embodiments the single liquid phase comprises one or more liquids that are hydrophilic. In some embodiments the single liquid phase comprises one or more liquids that are amphipathic. In some embodiments the single liquid phase comprises one or more liquids that are a combination of hydrophilic, lipophilic, and amphipathic liquids that yields a single liquid phase. Creams (e.g., Premarin® conjugated equine estrogens vaginal cream) containing at least two distinct liquid phases, such as an oil phase and a water phase, are not "monophasic" as intended herein. Rather, such creams are biphasic systems in which the drug is dispersed in one phase (generally a water phase) and the excipients are dispersed in another phase (generally an oil phase). This requires preparation of two separate phases and the use of emulsifiers for mixing the incompatible phases into a single composition (an emulsion). The phases remain physically and chemically distinct within the emulsion, which is often unstable upon variations in temperature or other physical parameters. In contrast with emulsions, monophasic systems comprise compatible components in a single phase. The term "monophasic" as used herein also encompasses solutions or suspensions in which components are dispersed within a single liquid phase. In some embodiments, the monophasic compositions described herein can comprise a molecular dispersion (a true solution) of one or more components. In some embodiments, the monophasic compositions described herein can comprise a molecular dispersion of at least a fraction of one or more components. Thus, a fraction rather than the entirety of an amount of a particular component can be present in a molecular dispersion. In some embodiments, the monophasic compositions described herein comprise a molecular dispersion of at least a fraction of at least one conjugated estrogen. In some embodiments, the monophasic compositions described herein can comprise one or more colloidal dispersions or coarse dispersions, depending on the particle size of the dispersed components as understood by one skilled in the art. In some embodiments, the monophasic compositions described herein can comprise any combination of molecular, colloidal, and coarse dispersions. In some embodiments, the monophasic compositions described herein can comprise a particular component as any combination of molecular, colloidal, and coarse dispersions. Components dispersed within the monophasic composition can be lipophilic, hydrophilic, amphipathic, or combinations thereof.

In some embodiments, the viscosity of the compositions can be adjusted to improve retention of the compositions at sites of application. Viscosity can be adjusted by excipients known in the art, including adhesion agents as described herein. In some embodiments, the viscosity can be greater than about 1.0 Poise (P) and less than about 30,000 P. In some embodiments, the viscosity of the composition at sites of application can be greater than about 1.0 P and less than about 20,000 P. In some embodiments, the viscosity of the composition at sites of application can be greater than about 2.5 P and less than about 10,000 P. In some embodiments, the viscosity of the composition at sites of application can be greater than about 10 P and less than about 5000 P. In some embodiments, the viscosity of the composition at sites of application can be greater than about 50 P and less than about 30,000 P. In some embodiments, the viscosity of the composition at sites of application can be greater than about 50 P and less than about 2,500 P. In some embodiments, the viscosity of the composition at sites of application can be greater than about 50 P and less than about 2,000 P. In some embodiments the viscosity of the composition at sites of application can be greater than about 90 P and less than about 30,000 P. In some embodiments, the viscosity of the composition at sites of application can be greater than about 90 P and less than about 2,500 P. In some embodiments, the viscosity of the composition at sites of application can be greater than about 90 P and less than about 2,000 P. In some embodiments, the viscosity of the composition at sites of application can be greater than about 250 P and less than about 2,000 P. In some embodiments, the viscosity of the composition at sites of application can be greater than about 500 P and less than about 2,000 P.

In some embodiments, the compositions of the present invention are bioadhesive, with prolonged retention at the site of application. In some embodiments, the compositions are bioadhesive, with prolonged retention when applied vaginally. In further embodiments, the compositions are applied vaginally with greater ease, with less dripping. In some embodiments, the compositions are applied vaginally and are associated with greater comfort due to less dripping. In some embodiments, the compositions are associated with greater comfort due to a soothing and emollient effect. In some embodiments, the compositions allow for greater patient compliance with prescribed administration procedures due to greater comfort.

In some embodiments, the compositions demonstrate improved spreadability as compared with existing formulations. In some embodiments, spreadability is measured by the percent area of spread (% spread) of the compositions as compared to the surface area of the site of administration. In some embodiments, spreadability is measured by the % spread of the compositions as compared to the estimated human vaginal surface area. In some embodiments, the compositions are capable of a % spread up to about 90% of the estimated human vaginal surface area. In some embodiments, the compositions are capable of a % spread up to about 80% of the estimated human vaginal surface area. In some embodiments, the compositions are capable of a % spread up to about 70%, 71%, or 72% of the estimated human vaginal surface area. In some embodiments, prolonged retention, bioadhesiveness, improved comfort, and combinations of such characteristics are associated with the % spread of the compositions.

In some embodiments, the compositions demonstrate physical stability as determined by characteristics including, but not limited to, appearance, pH, and viscosity at higher temperature and/or higher humidity for extended durations. In some embodiments, the compositions demonstrate chemical stability as determined by characteristics including, but not limited to, the chemical stability of conjugated estrogens at higher temperature and/or higher humidity. In some embodiments the chemical stability of conjugated estrogens in the compositions is determined by the ratio of equilin to estrone. In some embodiments, the ratio of equilin to estrone in the compositions remains substantially constant at higher temperature and/or higher humidity. In some embodiments, physical stability and/or chemical stability of the compositions is demonstrated over a period of greater than one year at higher temperature and/or higher humidity. In some embodiments, physical stability and/or chemical stability of the compositions is demonstrated over a period of one year at higher temperature and/or higher humidity. In some embodiments, physical stability and/or chemical stability of the compositions is demonstrated over a period of 6 months at higher temperature and/or higher humidity. In some embodiments, physical stability and/or chemical stability of the compositions is demonstrated over a period of 3 months at higher temperature and/or higher humidity. In some embodiments, physical stability and/or chemical stability of the compositions is demonstrated over a period of one month at higher temperature and/or higher humidity. In some embodiments, physical stability and/or chemical stability of the compositions is demonstrated over a period of one, two, three, or four weeks of higher temperature and/or higher humidity. In some embodiments, physical stability and/or chemical stability of the compositions is measured at 60° C. In some embodiments, physical stability and/or chemical stability of the compositions is measured at 40° C. and 75% relative humidity.

Various conjugated estrogens can be used within the scope of the compositions described herein. An estrogen is any of various natural steroids or synthetic steroids that stimulate the development of female secondary sex characteristics and promote the growth and maintenance of the female reproductive system; or any other compound that mimics the physiological effect of natural estrogens. Examples of estrogens are set forth in U.S. Pat. Nos. 5,908,638, 6,855,703, and 6,660,726, which are commonly assigned to the assignee of the present invention, the disclosures of which are incorporated by reference herein in their entireties. Suitable estrogens include estrone, 17α-estradiol, 17β-estradiol, equilin, 17α-dihydroequilin, 17β-dihydroequilin, equilenin, 17α-dihydroequilenin, 17β-dihydroequilenin, $\Delta^{8,9}$-dehydroestrone, 17α-$\Delta^{8,9}$-dehydroestradiol, 17β-$\Delta^{8,9}$-dehydroestradiol, ethinyl estradiol, estradiol valerate, 6-OH equilenin, 6-OH 17α-dihydroequilenin, 6-OH 17β-dihydroequilenin, and mixtures, and salts thereof, and the estrogen ketones and their corresponding 17α- and 17β-hydroxy derivatives. The term "conjugated" as described herein refers to various conjugates understood by those skilled in the art, including, but not limited to, sulfate esters, glucuronide esters, or mixed sulfate-glucuronide esters of an estrogen. In some embodiments, the estrogens are present as salts of estrogen conjugates. Pharmaceutically suitable salts can be various salts understood by those skilled in the art, including, but not limited to, sodium salts, calcium salts, magnesium salts, lithium salts, piperazine salts, and 2-amino-2-(hydroxymethyl)-1,3-propanediol (Tris) salts.

In some embodiments, the composition of the present invention comprises a conjugated estrogen such as, but not limited to, sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, or a combination thereof. In some embodiments, the composition of the present invention comprises a conjugated estrogen such as, but not limited to, sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, sodium Δ8,9-dehydroestrone sulfate, or a combination thereof. In some embodiments, the composition of the present invention comprises a conjugated estrogen such as, but not limited to, sodium ethinyl estradiol sulfate. In some embodiments, the conjugated estrogen is sodium ethinyl estradiol sulfate. In some embodiments, the conjugated estrogen is a mixture of 9 synthetic estrogens, such as, e.g., the mixture of estrogens found in CENESTIN® tablets, synthetic conjugated estrogens A (Duramed Pharmaceuticals, Inc., Pomona, N.Y.; see CENESTIN® prescribing information, revised February 2004). In some embodiments, the conjugated estrogen is a mixture of 10 synthetic estrogens; e.g., the mixture of estrogens found in ENJUVIA®, synthetic conjugated estrogens B (Endeavor Pharmaceuticals, Inc., Wilmington, N.C.; see ENJUVIA® package insert, revised May 4, 2004).

In some embodiments, the composition of the present invention comprises conjugated estrogens, wherein the conjugated estrogens consist of a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, and sodium 17β-dihydroequilenin sulfate. In some embodiments, the composition of the present invention comprises conjugated estrogens, wherein the conjugated estrogens consist of a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate.

In some embodiments, the composition of the present invention consists essentially of a conjugated estrogen, including one or more conjugated estrogens. In some embodiments, the composition of the present invention consists essentially of conjugated estrogens, wherein the conjugated estrogens consist of a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, and sodium 17β-dihydroequilenin sulfate. In some embodiments, the composition of the present invention consists essentially of conjugated estrogens, wherein the conjugated estrogens consist of a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate.

In some embodiments, the composition of the present invention is substantially devoid of impurities present in naturally derived conjugated equine estrogens, including, but not limited to, indican, sulfated benzyl alcohol, hippuric acid, benzoic acid, and creatinine and as described in U.S. Pat. No. 6,855,703.

In some embodiments, the composition of the present invention is substantially free of ethanol.

In some embodiments, the composition of the present invention further comprises a pharmaceutically acceptable excipient. As used herein, "excipient" refers to a component, or mixture of components, that is used in the formulation of the compositions of the present invention to give desirable characteristics to the composition. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problematic complications over the desired duration of treatment commensurate with a reasonable benefit/risk ratio. In some embodiments, the term "pharmaceutically acceptable" means approved by a regulatory agency of the Federal or a state government or listed in the U.S. Pharmacopeia or other generally recognized international pharmacopeia for use in animals, and more particularly in humans. Various pharmaceutically acceptable excipients can be used. In some embodiments, the pharmaceutically acceptable excipient can be, but is not limited to, an alkaline agent, a stabilizer, an adhesion agent, a solvent, a surfactant, a humectant, a buffering agent, a filler, an emollient, or combinations thereof. Excipients in addition to those discussed herein can include excipients listed in, though not limited to, Garg, S. et al. *Pharm. Tech.* 25(2):1-14 (2001) and references cited therein and in *Remington: The Science and Practice of Pharmacy*, 21$^{st}$ ed. (2005). Inclusion of an excipient in a particular classification herein (e.g., "solvent") is intended to illustrate rather than limit the role of the excipient. A particular excipient can actually fall within multiple classifications.

The term "alkaline agent" refers to any substance utilized for its alkaline properties and includes any pharmaceutically acceptable material that can increase the pH of a medium. In some embodiments the alkaline agent is an inorganic base. In some embodiments, the alkaline agent is an inorganic base such as hydroxides, oxides, or combinations thereof of alkali metals, alkaline earth metals, or combinations thereof. Suitable alkali metals and alkaline earth metals include, but are not limited to, lithium, potassium, calcium, magnesium, and sodium. In some embodiments, the alkaline agent is an organic base. In some embodiments, the alkaline agent is an organic base such as a primary amine, a secondary amine, a tertiary amine, ammonium hydroxide, or combinations thereof. In some embodiments, the alkaline agent is an organic base such as trimethylamine, triethylamine, triethanolamine, or ammonium hydroxide.

The pH of the composition of the invention can be physiologically compatible and/or sufficient to maintain stability of the composition. In some embodiments, the composition of the present invention can have a pH of about 5 to about 9, or a pH of about 6 to about 8. Pharmaceutically acceptable acids and bases known in the art can be utilized to adjust pH. In some embodiments, pharmaceutically acceptable acids and bases include sodium hydroxide and hydrochloric acid.

Stability of a pharmaceutical composition is one factor determining the frequency of application required to elicit a therapeutic effect. Given the latter, a more stable pharmaceutical composition for estrogen replacement therapy would be particularly beneficial. Various stabilizers can be used in the present invention. The term "stabilizer" refers to any substance that keeps a component of the composition chemically stable. Alternatively, the term "stabilizer" refers to any substance that slows or retards the degradation or alteration of a component of the composition. For example, a stabilizer can protect an estrogen from instability caused by light, moisture, heat, hydrolysis, or oxidation. In some embodiments, the stabilizer is lipophilic. In some embodiments, the stabilizer is hydrophilic. In some embodiments, the stabilizer can be, but is not limited to, methyl paraben, propyl paraben, t-butyl hydroquinone, butylated hydroxyanisole (BHA), butylated hydroxytoluene (BHT), ascorbic acid and its esters, vitamin E and its esters (e.g., vitamin E acetate), sodium bisulfite, sodium metabisulfite, 3-dehydroshikimic acid (DHS), tocopherols and their esters, alkyl gallates, chelating agents, EDTA (ethylenediaminetetraacetic acid; edetate disodium), citric acid, benzyl alcohol, or combinations thereof. In some embodiments, the stabilizer can be methyl paraben, propyl paraben, edetate disodium, butylated hydroxyanisole, butylated hydroxytoluene, or combinations thereof.

The term "adhesion agent" refers to a substance, or mixture of substances, added to improve retention and/or bioavailability of the compositions. The adhesion agent can be hydrophilic (e.g., various carbomers, including Carbopol® 934P and 974P, as well as carboxymethylcellulose, hydroxypropylmethylcellulose, including hypromellose 2208, alginate, and polyethylene glycol). In some embodiments, the adhesion agent has low hydrophilic-lipophilic balance (HLB). In some embodiments, the HLB value is less than 7. In some embodiments, the HLB value is less than 5. In some embodiments, the HLB value is about 4. Examples of suitable adhesion agents include, but are not limited to, hydrogenated vegetable oil, ethyl alcohol, cetyl alcohol, cetyl esters wax, microcrystalline wax, paraffin, stearyl alcohol, lauryl alcohol, myristyl alcohol, cetostearyl alcohol, white wax, yellow wax, beeswax, candelilla wax, cotton wax, carnauba wax, bayberry wax, rice-bran wax, starch, methylcellulose, microcrystalline cellulose, and combinations thereof. In some embodiments, the adhesion agent is a mixture of cetyl esters wax, cetyl alcohol, and beeswax.

The term "solvent" refers to any substance capable of dissolving or dispersing one or more of the conjugated estrogens or excipients of the present invention. The solvent can be aqueous or non-aqueous. The solvent can be hydrophilic, lipophilic, or amphipathic. In some embodiments a solvent is amphipathic and is associated with additional lipophilic or hydrophilic solvents in a monophasic composition as described herein. In some embodiments, the solvent is water, a polyol (e.g., glycerol), glyceryl esters of fatty acids, or lauryl macrogolglycerides (e.g., Gelucire®-based 44/14).

The term "surfactant" refers to any substance that lowers the surface tension of a pharmaceutical composition of the invention. In some embodiments, the surfactant includes, but is not limited to, sodium lauryl sulfate, polysorbate 80, poloxamer, lauryl macrogolglycerides, polyoxyethylene alkyl ethers, and combinations thereof.

The term "humectant" refers to any substance that promotes retention of moisture in the composition of the present invention. In some embodiments, the humectant includes, but is not limited to, polyethylene glycol, propylene glycol, glycerin, polyol, polyol derivatives, and combinations thereof.

The term "buffering agent" refers to any substance capable of neutralizing both acids and bases and thereby maintaining the desired pH of the composition of the present invention. In some embodiments, the buffer can be, but is not limited to, Tris buffers (Tris EDTA (TE), Tris acetate (TAE), Tris phosphate (TPE), Tris glycine), phosphate buffers (e.g., sodium phosphate, potassium phosphate), bicarbonate buffers, acetate buffers (e.g., sodium acetate), ammonium buffers, citrate buffers, and derivatives and combinations thereof. In some embodiments, an organic acid buffer is used. In some embodiments, an acetate buffer, a phosphate buffer, or a citrate buffer can be used. In some embodiments, a zwitterionic buffer can be used. In some embodiments, the buffering agent is a phosphate buffer (e.g., sodium phosphate dibasic).

As defined herein, an "emollient" is a substance that moisturizes and increases the pliability of a treated epithelium. In some embodiments, the emollient can be, but is not limited to, lanolin, isopropyl myristate, palmitate, oleyl alcohol, beeswax, mineral oil, silicone oil, or combinations thereof.

As defined herein, a "filler" is a substance used to give bulk to the composition without chemically reacting with the conjugated estrogens of the present invention. Fillers are known to those in the art, see e.g., *Remington: The Science and Practice of Pharmacy*, 21$^{st}$ ed. (2005).

Acceptable excipients associated with a hydrophilic phase of the described monophasic compositions include, but are not limited to water, glycerin, polyethylene glycol, polyols, alcohols, and combinations thereof.

Acceptable excipients associated with a lipophilic phase of the described monophasic compositions include, but are not limited to monoglycerides, diglycerides, triglycerides, esters of glycerol (1,2,3-propanetriol) and fatty acids and include lipophilic liquids such as oils. In some embodiments, the pharmaceutical compositions described herein comprise glyceryl esters of fatty acids comprised of hydrocarbon chain lengths of 4 or more carbons. In some embodiments, each hydrocarbon chain can contain 4 to 36 carbon atoms. In some embodiments, each hydrocarbon chain can contain 4 to 24 carbon atoms. In some embodiments, the hydrocarbon chains can contain a variety of functional groups. In some embodiments, the hydrocarbon chain can be branched. In some embodiments, the hydrocarbon chains are unsaturated or polyunsaturated. In some embodiments, the hydrocarbon chains are saturated. The degree of saturation can affect the physical state, for example viscosity, of the lipophilic excipient. In some embodiments, the lipophilic excipient is lauric acid, myristic acid, palmitic acid, stearic acid, behenic acid, oleic acid, 12-hydroxystearic acid, undecylenic acid, tall acid, lanolin fatty acid, isostearic acid, linoleic acid, linolenic acid, or combinations thereof. In some embodiments, the lipophilic excipient can be, but is not limited to, vegetable, nut, or seed oils (e.g., almond oil, castor oil, coconut oil, corn oil, cotton seed oil, jojoba oil, linseed oil, grape seed oil, rape seed oil, mustard oil, olive oil, palm and palm kernel oil, peanut oil, safflower oil, sesame oil, soybean oil, sunflowerseed oil, crambe oil, wheat germ oil, or cocoa butter), hydrocarbon or petroleum oils (e.g., petrolatum, mineral oil, or liquid paraffin). In some embodiments, the oil is not an ester of glycerol, e.g., mineral oil and silicone oil.

The amount of active agent or agents in a dosage form can vary. The exact dosage amount can be selected depending upon the needs of the patient to which the active agent is being administered, as determined by a relevant person. In some embodiments, one of skill in the art can perform pharmacokinetic studies and use the results of the study to adjust the dosage amount for a female, or a group of females, to a suitable level. In some embodiments, one of skill in the art can determine an appropriate dosage amount based on varying dosage amounts and comparing to symptomatic relief. In some embodiments, appropriate animal studies can be performed to determine an appropriate dosage amount. A "relevant person" as used herein, includes, for example, a physician, physician assistant, nurse practitioner, pharmacist, and customer service representative.

In some embodiments, the composition of the present invention is in a dosage form, wherein the dosage form comprises conjugated estrogen in an amount comprising about 0.1 mg/dose to about 15 mg/dose, about 0.5 mg/dose to about 12 mg/dose, or about 1.0 mg/dose to about 10.0 mg/dose of conjugated estrogen. In some embodiments, the composition of the present invention is in a dosage form, wherein the dosage form comprises a total amount of the pharmaceutical composition in an amount comprising about 50 mg/dose to about 7.5 g/dose, about 75 mg/dose to about 6 g/dose, about 100 mg/dose to about 5 g/dose, about 100 mg/dose to about 3 g/dose, about 100 mg/dose to about 1 g/dose, or about 100 mg/dose to about 500 mg/dose of the dosage form. In some embodiments, the use of smaller amounts of locally administered pharmaceutical compositions for estrogen replacement therapy are desirable, wherein the total amount of the pharmaceutical composition is an amount comprising about 50 mg/dose to about 500 mg/dose of the dosage form. In some embodiments, the dosage form is administered in a smaller volume of product per dose.

In some embodiments, the composition of the present invention is in a concentrated dosage form. In some embodiments the composition of the present invention is in a concentrated dosage form, wherein the concentrated dosage form comprises about 50 mg/dose to about 500 mg/dose of total composition and about 1 mg/dose to about 10 mg/dose of conjugated estrogen. In some embodiments the composition of the present invention is in a concentrated dosage form, wherein the concentrated dosage form comprises about 500 mg/dose of total composition and about 1.0 mg/dose to about 10 mg/dose of conjugated estrogen. In some embodiments the composition of the present invention is in a concentrated dosage form, wherein the concentrated dosage form comprises about 500 mg/dose of total composition and about 1.25 mg/dose of conjugated estrogen. In some embodiments, unless a specific estrogen is identified, amounts of "conjugated estrogens" refer to a summation of the amounts of three estrogens: sodium 17α-dihydroequilin sulfate, sodium estrone sulfate, and sodium equilin sulfate. In some embodiments, the dosage form comprises a conjugated estrogen equivalent to an amount of sodium estrone sulfate comprising about 25 μg/dose to about 5 mg/dose, about 50 μg/dose to about 5 mg/dose, about 50 μg/dose to about 2.5 mg/dose, about 50 μg/dose to about 1 mg/dose, and about 50 μg/dose to about 500 μg/dose sodium estrone sulfate. In some embodiments, the dosage form comprises a conjugated estrogen equivalent to an amount of sodium equilin sulfate comprising about 15 μg/dose to about 5 mg/dose, about 30 μg/dose to about 5 mg/dose, about 30 μg/dose to about 3 mg/dose, about 30 μg/dose to about 1 mg/dose, and about 30 μg/dose to about 500 μg/dose sodium equilin sulfate. In some embodiments, the dosage form comprises a conjugated estrogen equivalent to an amount of sodium 17-β estradiol sulfate comprising about 1 μg/dose to about 5 mg/dose, 100 μg about 15 μg/dose to about 5 mg/dose, about 30 μg/dose to about 5 mg/dose, about 30 μg/dose to about 3 mg/dose, about 30 μg/dose to about 1 mg/dose, about 30 μg/dose to about 500 μg/dose, and about 1 μg/dose to about 100 μg/dose sodium 17-β estradiol sulfate. In some embodiments, the dosage form comprises a conjugated estrogen equivalent to an amount of sodium Δ8,9-dehydroestrone sulfate comprising about 0.2 μg/dose to about 100 μg/dose, about 0.2 μg/dose to about 50 μg/dose, about 0.3 μg/dose to about 25 μg/dose, about 0.4 μg/dose to about 10 μg/dose, or about 0.4 μg/dose to about 2 μg/dose of sodium Δ8,9-dehydroestrone sulfate. In some embodiments, the composition of the present invention is in a dosage form, wherein the dosage form comprises about 1.25 mg/dose of conjugated estrogen.

In some embodiments, the compositions of the present invention demonstrate better diffusion and/or higher absorption of conjugated estrogens at the site of administration or across cultured tissue as compared with existing formulations, such as but not limited to, conjugated equine estrogen cream formulations. In some embodiments, the compositions demonstrate better diffusion of estrone and/or equilin at the site of administration or across cultured tissue. In some embodiments, the compositions demonstrate better diffusion of conjugated estrogens across vaginal tissue. In some embodiments, the percent diffusion of estrone from the compositions across vaginal tissue is from about 25% to about 90% at 24 hours. In some embodiments, the percent diffusion of estrone from the compositions across vaginal tissue is from about 30% to about 90% at 24 hours. In some embodiments, the percent diffusion of estrone from the compositions across vaginal tissue is from about 40% to about 90% at 24 hours. In some embodiments, the percent diffusion of estrone from the compositions across vaginal tissue is from about 50% to about 90% at 24 hours. In some embodiments, the compositions of the present invention demonstrate better diffusion of conjugated estrogens across a non-living membrane as compared with existing cream formulations. In some embodiments, the compositions demonstrate better of estrone and/or equilin diffusion across a non-living membrane. In some embodiments, the non-living membrane is a cellulose acetate membrane. In some embodiments, the percent diffusion of estrone from the compositions across a cellulose acetate membrane is 100% at 6 hours. In some embodiments, the percent diffusion of estrone from the compositions across a cellulose acetate membrane is from about 60% to about 90% at 6 hours. In some embodiments, the percent diffusion of estrone from the compositions across a cellulose acetate membrane is from about 80% to about 90% at 6 hours. In some embodiments, the compositions demonstrating better diffusion and/or higher absorption permit a smaller dose and/or a reduced frequency of dosing.

Various types of conjugated estrogens of the present invention can be present in the pharmaceutical composition in varying amounts. In some embodiments, the percentage of the estrogens can be found within about the ranges listed in Table 1.

TABLE 1

| Estrogens* | Range A | Range B | Range C | Range D |
|---|---|---|---|---|
| 17α-Estradiol | 0%-99% | 0.5%-20% | 1%-11% | 2%-10% |
| 17α-Dihydroequilin | 0%-99% | 5%-30% | 7%-25% | 10%-21% |
| 17β-Dihydroequilin | 0%-99% | 0%-10% | 0.5%-7% | 0.1%-5% |
| Estrone | 0%-99% | 25%-80% | 40%-70% | 50%-64% |
| Equilin | 0%-99% | 10%-50% | 15%-35% | 20%-32% |
| 17β-Estradiol | 0%-99% | 0%-7% | 0.05%-4% | 0.1%-3.5% |
| 17α-Dihydroequilenin | 0%-99% | 0%-7% | 0.05%-5% | 0.1%-4% |
| 17β-Dihydroequilenin | 0%-99% | 0%-7% | 0.05%-5% | 0.1%-4% |
| Equilenin | 0%-99% | 0%-15% | 0.1%-10% | 0.1%-6.5% |
| Δ8,9-dehydroestrone | 0%-99% | 0.1%-10% | 1%-10% | 1%-8% |

*all estrogens reported as the sodium salts of 3-monosulfate esters

As shown in Table 1, various combinations and amounts of conjugated estrogens can be used in the present invention. In some embodiments, the composition of the present invention is in a dosage form, wherein the dosage form comprises about 1 mg/dose to about 10 mg/dose of conjugated estrogens, wherein the conjugated estrogens consist of (a) about 2% to about 10% by weight sodium 17α-estradiol sulfate; (b) about 10% to about 21% by weight sodium 17α-dihydroequilin sulfate; (c) about 0.1% to about 5% by weight sodium 17β-dihydroequilin sulfate; (d) about 50% to about 64% by weight sodium estrone sulfate; (e) about 20% to about 32% by weight sodium equilin sulfate; (f) about 0.1% to about 3.5% by weight sodium 17β-estradiol sulfate; (g) about 0.1% to about 4% by weight sodium 17α-dihydroequilenin sulfate; (h) about 0.1% to about 4% by weight sodium 17β-dihydroequilenin sulfate; (i) about 0.1% to about 6.5% by weight sodium equilenin sulfate; and (j) about 1% to about 8% by weight sodium Δ8,9-dehydroestrone sulfate; or an amount of a mixture of conjugated estrogens that provides an estrogenic effect equivalent to that produced by the about 1 mg/dose to about 10 mg/dose of conjugated estrogens as defined in (a)-(j).

In some embodiments, the amount of a particular estrogen can be in the ranges specified in Table 2.

TABLE 2

| | Dosage Amounts (μg/dosage form) | | |
|---|---|---|---|
| Estrogen* | Range E | Range F | Range G |
| 17α-Estradiol | 0-2500 | 1.0-17.5 | 43.75-87.5 |
| 17α-Dihydroequilin | 0-2500 | 30-475 | 125-237.5 |
| 17β-Dihydroequilin | 0-2500 | 1.5-87.5 | 6.25-43.75 |
| Estrone | 0-2500 | 153-1550 | 637.5-775 |
| Equilin | 0-2500 | 60-775 | 250-387.5 |
| 17β-Estradiol | 0-2500 | 1.5-50 | 6.25-25 |
| 17α-Dihydroequilenin | 0-2500 | 0.6-125 | 2.5-62.5 |
| 17β-Dihydroequilenin | 0-2500 | 0.3-37.5 | 1.25-18.75 |
| Equilenin | 0-2500 | 1.5-162.5 | 6.25-81.25 |
| Δ8,9-dehydroestrone | 0-2500 | 1.25-125 | 12.5-125 |

*All estrogens reported as the sodium salts of the 3-monosulfate esters.

The ranges listed in Table 2 for each estrogen are mutually exclusive from the ranges for the other estrogens.

The listed estrogens, as well as other estrogens, vary in potency from each other. The ranges given above are for the specified estrogen; however, if a different estrogen is employed, adjustments in the amount employed, based on the relative potency, can be made and are well known in the art. The correlations in potency between various estrogens are known. See, for example, EP 0 253 607, which is hereby incorporated in its entirety by reference. Equivalent concentrations of estrogens can be determined using either in vitro or in vivo assay methods (Kuhl, H., *Drugs* 51:188-215 (1996); Philibert, D., et al., *Gynecol. Endocrinol.* 13:316-326 (1999); and Lundeen, S., et al., *J. Steroid Biochem. Molec. Biol.* 78:137-143 (2001)). When in vitro receptor binding studies are performed to determine relative potency, the unconjugated forms of an estrogen should be used. See also, for example, Dickey, R. P., "Contraceptive Therapy," *OBG Management Supplement* (October 2000), pp. 2-6. As described herein, "relative potency," "equivalent amount," or "amount equivalent to" can be determined by a method described by Mandel et. al. (*J. Clin. Endocrinol. Metabol.* 57:133-139 (1983)). Each of these documents is hereby incorporated by reference in its entirety.

As used herein, "about" refers to plus or minus 10% of the indicated number. For example, "about 10%" indicates a range of 9% to 11%.

Methods of Treating Menopausal Conditions

In some embodiments, the present invention is directed to a method of treating a condition that benefits from estrogen replacement therapy in a female in need thereof, the method comprising administering to the female a monophasic pharmaceutical composition comprising a conjugated estrogen and a lipophilic or hydrophilic excipient. In some embodiments, the method comprises administering to the female a composition with a viscosity greater than about 1 Poise and less than about 30,000 Poise. In some embodiments, the present invention is directed to a method of treating a menopausal condition in a female. In some embodiments, the pharmaceutical composition is administered transmucosally. In some embodiments, the pharmaceutical composition is administered transmucosally comprising vaginal administration. In some embodiments, the pharmaceutical composition is administered transmucosally comprising oral administration.

The terms "treat" and "treatment" refer to both therapeutic treatment and prophylactic or preventative measures, wherein the object is to prevent, inhibit, reverse or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset, or slowing, of condition, disorder or disease progression; amelioration of the condition, disorder or disease state, remission (whether partial or total); or enhancement or improvement of the condition, disorder or disease. Treatment also includes, but is not limited to, eliciting a cellular response that is clinically significant, without excessive levels of side effects. In some embodiments, treatment involves transmucosal administration. In some embodiments, transmucosal administration involves vaginal administration. In some embodiments, transmucosal administration involves oral administration.

"Female" refers to any animal classified as a mammal which menstruates, including primates, e.g., humans. "Female" also refers to other nonhuman mammals, e.g., domestic and farm animals, and zoo, sports, and companion animals such as household pets and other domesticated animals such as, but not limited to, cattle, sheep, ferrets, swine, horses, rabbits, goats, dogs, cats, and the like. In some embodiments, companion animals are dogs and cats.

Treatment can occur over any pharmaceutically acceptable period. In some embodiments, the pharmaceutical composition is administered at least once. In some embodiments, the pharmaceutical composition is administered at least once per day. In some embodiments, the pharmaceutical composition is administered multiple times per day, for example, at least twice per day. In some embodiments, the pharmaceutical composition is administered at least once daily for at least 2 consecutive days. In some embodiments, the pharmaceutical composition is administered at least twice per week for at least 1 week. In some embodiments, the pharmaceutical composition is administered at least once daily for at least 7 consecutive days. In some embodiments, the pharmaceutical composition is administered at least twice per week for at least 2 weeks. In some embodiments, the pharmaceutical composition is administered (a) at least once daily for at least 2 consecutive days, then (b) at least twice per week for at least 2 weeks. In some embodiments, the pharmaceutical composition is administered (a) at least once daily for at least 7 consecutive days, then (b) at least twice per week for at least 2 weeks. In some embodiments, the pharmaceutical composition is administered (a) at least once daily for 2 to 13 consecutive days, then (b) at least twice per week for at least 2 weeks.

In some embodiments, the method of treatment can be divided into two stages. The "starter" stage encompasses daily administration of the pharmaceutical composition. In some embodiments, the starter stage encompasses administration of the pharmaceutical composition at least once daily for 7 consecutive days. In some embodiments, the starter stage encompasses administration of the composition of the present invention daily for at least 2 to 13 consecutive days. In some embodiments, the starter stage encompasses administration of the composition of the present invention daily for at least 5 to 13 consecutive days. In some embodiments, the composition is administered at least once daily for at least 7 consecutive days. In some embodiments, treatment of a female by administering a starter stage is preferable for a female who has not recently been treated for a menopausal condition using any other hormone therapy. In some embodiments, treatment of a female by administering a starter stage is preferable for a female who has previously been on hormone therapy, but has stopped taking the therapy for such a time as to allow the vaginal cytology of the female to revert to a substantially post-menopausal state. In some embodiments, treatment of a female by administering a starter stage is preferable for a female whose vaginal epithelial cytology is in a menopausal state.

The "maintenance" stage encompasses administration of the pharmaceutical composition at least twice per week for at least two weeks. In some embodiments, the maintenance stage follows the starter stage. In some embodiments, the maintenance stage comprises administering the composition of the present invention for two weeks. However, in some embodiments, the maintenance stage can be longer in duration. For example, the maintenance stage can continue until the menopausal condition being treated no longer requires treatment. In some embodiments, the maintenance stage continues for 2 weeks to 2 years. In some embodiments, the maintenance stage continues for 2 weeks to 1 year. In some embodiments, the maintenance continues for 3 weeks to 4 weeks. In some embodiments, the maintenance stage continues for 3.5 weeks. In some embodiments, treatment of a female by administering the maintenance stage without a starter stage is preferable for a female who has recently been treated for a menopausal condition using hormone therapy. In some embodiments, treatment of a female by administering the maintenance stage without a starter stage is preferable for a female whose vaginal epithelial cytology is in a premenopausal state.

The term "once daily" refers to administration of a composition of the present invention once during a 24 hour period. In some embodiments, the composition is administered once per day. In some embodiments, the composition is administered twice per day. In some embodiments, the composition is administered more than twice per day.

The present invention is suitable for treatment of various menopausal conditions. The term "menopausal condition" relates to conditions associated with menopause, or to the period of natural cessation of menstruation. Additionally, the term "menopausal condition" also relates to conditions related to peri-menopause, post menopause, or oophorectomized women. Thus, the term menopausal condition is not limited to females that are undergoing menopause, but also women who are undergoing peri-menopause or post-menopause, women who have been bilaterally oophorectomized, or women whose endogenous sex hormone production has been suppressed by pharmaceutical chemical compositions, e.g., GnRH agonists such as leuprolide-acetate sold under the tradename LUPRONE® (TAP Pharmaceutical Products, Inc) or goserilin acetate, sold under the tradename ZOLADEX® (AstraZeneca). The phrase "vaginal epithelial cytology is in a pre-menopausal state" refers to the state of a vaginal epithelial of a woman who has not yet entered perimenopause or menopause. The phrase "vaginal epithelial cytology is in a menopausal state" refers to the state of a vaginal epithelial of a woman who is in menopause and is not taking any form of hormone replacement therapy. The state of the vaginal epithelial can be evaluated as described by Mandel et al (*J. Clin. Endocrinol. Metabol.* 57: 133-139 (1983)).

Various menopausal conditions can exist. In some embodiments, a menopausal condition can be, but is not limited to, vaginal dryness, pain during intercourse (dyspareunia), increased risk of infections, inability to control urination (incontinence), increased frequency of urinary infections, vaginal atrophy, kraurosis vulvae, hot flashes and night sweats, fatigue, emotional changes (mood swings and changes in sexual interest), sleep disturbances (insomnia), drier skin and hair, increased growth of facial and body hair, aches and pains in the joints, headaches, palpitations (rapid, irregular heart beats), vaginal itching, osteoporosis, osteopenia, and generalized itching.

In some embodiments, the pharmaceutical composition can be administered vaginally by contacting the pharmaceutical composition with the vaginal tract of the female being treated. In some embodiments, the pharmaceutical composition can be administered orally by contacting the pharmaceutical composition with the oral cavity of the female being treated. In some embodiments, once the pharmaceutical composition is administered, the estrogens act locally (for example, on the vaginal or oral epithelia, i.e., non-systemically). In some embodiments, once the pharmaceutical composition is administered, the estrogens act systemically on the female being treated. Thus, in some embodiments, administration of the pharmaceutical composition of the present invention provides systemic treatment of a menopausal condition. In some embodiments, administration of the pharmaceutical composition of the present invention provides both systemic and local treatment of a menopausal condition.

In some embodiments, administration of the composition of the present invention can produce a pulsatile pharmacokinetic delivery profile of estrogens. In these embodiments, after administration of the composition of the present invention, an initial increase in the plasma concentration of estrogens occurs. Blood plasma concentration levels of estrogens then peak, after which there is a decrease in the plasma concentration of estrogens in the female being treated. Upon administration of another dose of the composition, the plasma concentration of estrogen again increases, peaks, and then decreases. The term "pulsatile pharmacokinetic profile" refers to the cyclic increase, peak, and decrease of plasma concentrations of estrogens. In some embodiments, the pulsatile pharmacokinetic profile is reduced upon repeated administration of the composition of the present invention. That is, the peak plasma concentration of estrogens is less than the peak plasma concentration of estrogens achieved by the previous administration of the composition of the present invention. In some embodiments, after repeated administration of the estrogens, an essentially steady state pharmacokinetic profile is reached, resulting in a relatively constant pulsatile pharmacokinetic profile. That is, the peak at steady state following administration of the composition of the present invention remains relatively constant upon administration of additional doses of the composition of the present invention. In some embodiments, after two weeks, the pulsatile delivery of estrogens is at steady state. In some embodiments, after four weeks, the pulsatile delivery of estrogens is at steady state.

Kits, Dosage Forms, and Applicators

In some embodiments, the present invention is also directed to a kit or an applicator comprising a monophasic pharmaceutical composition comprising a conjugated estrogen and a hydrophilic or lipophilic excipient.

In some embodiments, the present invention is directed to a kit comprising a dosage form comprising the pharmaceutical compositions of the present invention. As used herein, the term "dosage form" refers to a dosage of a composition of the present invention which is administered to a patient in about a 24 hour period. In some embodiments, multiple dosage forms can be contained in one kit. In some embodiments, one or more dosage forms are separately packaged from other dosage forms, e.g., individual dosage forms. In some embodiments, the dosage form is a capsule containing a pharmaceutical composition described herein. In some embodiments, the dosage form comprises a membrane or envelope that surrounds the pharmaceutical composition. In some embodiments, the dosage form is a vaginal sachet containing the pharmaceutical composition. In some embodiments, the dosage form comprises an amount of a pharmaceutical composition as described herein contained in an applicator. In some embodiments, the dosage form comprises an amount of a pharmaceutical composition as described herein contained in a vaginal applicator. In some embodiments, the dosage form comprises an amount of a pharmaceutical composition as described herein contained in an oral applicator. In some embodiments, the oral applicator comprises an amount of a pharmaceutical composition as described herein as a spray. In some embodiments, the applicator is used to administer a single unit-dose of a pharmaceutical composition as described herein.

Various numbers of dosage forms can be contained in a single kit. In some embodiments, the kit can comprise from 1 to about 60 or 1 to about 30 dosage forms comprising the pharmaceutical compositions as described herein. In some embodiments, the kit comprises at least 2 dosage forms comprising the pharmaceutical compositions as described herein.

In some embodiments, the kit comprises at least 7 dosage forms comprising the pharmaceutical compositions as described herein. For example, the kit can comprise dosage forms sufficient for initial therapy (e.g., one dose per day for 7 days). In some embodiments, the kit comprises at least 13 dosage forms comprising a composition of the present invention. In some embodiments, the kit can comprise 13 to 14 dosage forms comprising the pharmaceutical compositions as described herein. For example, the kit can comprise dosage forms sufficient for initial therapy plus the remainder of the month (e.g., one dose per day for 7 days plus one dose per day, 2 days per week for the remainder of the month (6-7 doses)). In some embodiments, the kit can comprise at least 8 dosage forms comprising the pharmaceutical compositions as described herein. In some embodiments, the kit can comprise 8 to 9 dosage forms comprising the pharmaceutical compositions as described herein. For example, the kit can comprise dosage forms sufficient for administration 2 days per week for a month. One of skill in the art could produce additional kits which provide a suitable number of dosage forms within the scope of the invention. For example, a kit comprising dosage forms sufficient for two to six months.

In some embodiments, the present invention is directed to a kit comprising vaginal or oral applicators, wherein each of the vaginal or oral applicators comprises a pharmaceutical composition of the present invention. In some embodiments, the vaginal or oral applicators are disposable. The term "disposable" refers to applicators that are intended to be used once, and then discarded. In some embodiments, the applicators are used once to administer a single-unit dose, and then discarded. In some embodiments, release of a dose requires a subject to apply pressure to the applicator, for example, by squeezing, pressing, pushing, or otherwise directly manipulating the applicator to cause the release of a single-unit dose of the monophasic pharmaceutical composition. The disposable applicators can come in any shape and size suitable for applying the pharmaceutical composition of the present invention into a vaginal tract or oral cavity. For example, in some embodiments, the applicator is a syringe. In some embodiments, the applicator is a squeezable tube shaped to allow administration of the pharmaceutical composition directly to the vaginal tract. In some embodiments, the applicator comprises a spray, solution, suspension, or other composition of the present invention for delivery to the oral cavity. Alternatively, the kit can comprise a single container comprising multiple doses of the composition. For example, the kit can be a container containing a month's supply of the pharmaceutical composition. In some embodiments, the kit can comprise one or more applicators to apply the pharmaceutical composition from the container comprising multiple doses. In some embodiments, the kit can comprise one or more devices used to measure an appropriate amount of the composition of the present invention.

The applicator can comprise various amounts of conjugated estrogens. In some embodiments, each applicator comprises a single dosage form of the composition. For example, in some embodiments, the applicator comprises a conjugated estrogen equivalent to about 50 µg to about 5 mg of sodium estrone sulfate. In some embodiments, the applicator comprises a conjugated estrogen equivalent to about 30 µg to about 3 mg of sodium equilin sulfate. In some embodiments, the applicator comprises a conjugated estrogen equivalent to about 1 µg to about 100 µg of sodium 17β-estradiol sulfate.

The kits of the present invention can contain various amounts of vaginal or oral applicators. In some embodiments, the applicators are disposable. In some embodiments, the kit comprises 1 to about 30 disposable applicators. In some embodiments, the kit comprises about 5 to about 20 applicators. In some embodiments, the kit comprises at least 2 applicators. In some embodiments, the kit comprises at least 7 applicators. In some embodiments, the kit comprises at least 8 applicators. In some embodiments, the kit comprises 8 to 9 applicators. In some embodiments, the kit comprises at least 13 applicators. In some embodiments, the kit comprises 13 to 14 applicators. In some embodiments, the applicators in a kit comprise one or more of the ingredients of a pharmaceutical composition as described herein.

The kit can include one or more containers filled with one or more of the ingredients of a pharmaceutical composition of the invention. In some embodiments, a pharmaceutical composition of the present invention is stored in a container essentially impermeable to oxygen. In some embodiments, the composition is purged with an inert gas, e.g., nitrogen gas.

Optionally associated with such container(s) can be a notice or printed instructions. For example, such printed instructions can be in a form prescribed by a governmental agency regulating the manufacture, use, or sale of pharmaceuticals or biological products, which notice reflects approval by the agency of the manufacture, use, or sale for human administration to treat a menopausal condition. In some embodiments, the kit further comprises printed matter, which, e.g., provides information on the use of the composition to treat a menopausal condition, a pre-recorded media device which, e.g., provides information on the use of the applicator or pharmaceutical composition to treat a menopausal condition, or a planner.

"Printed matter" can be, for example, one of a book, booklet, brochure, or leaflet. The printed matter can describe the use of the applicator or pharmaceutical composition of the present invention for the treatment of a menopausal condition. Possible formats include, but are not limited to, a bullet point list, a list of frequently asked questions (FAQ), or a chart. Additionally, the information to be imparted can be illustrated in non-textual terms using pictures, graphics, or other symbols.

"Pre-recorded media device" can be, for example, a visual media device, such as a videotape cassette, a DVD (digital video disk), filmstrip, 35 mm movie, or any other visual media device. Alternately, pre-recorded media device can be an interactive software application, such as a CD-ROM (compact disk-read only memory) or floppy disk. Alternately, pre-recorded media device can be, for example, an audio media device, such as a record, audiocassette, or audio compact disk. The information contained on the pre-recorded media device can describe the use of the applicator or pharmaceutical composition of the present invention for the treatment of a menopausal condition.

A "planner" can be, for example, a weekly, a monthly, a multi-monthly, a yearly, or a multi-yearly planner. The planner can be used as a diary to monitor dosage amounts, to keep track of dosages administered, or to prepare for future events wherein taking a regularly administered pharmaceutical composition of the present invention may be difficult. Alternately, the planner can be a calendar which will provide a means to monitor when a dosage has been taken and when it has not been taken. This type of planner will be particularly useful for patients having unusual schedules for administering medication to themselves. Additionally, the planner can be useful for the elderly, or other patient group who may administer medication to themselves and may become forgetful. One skilled in the art will appreciate the variety of planning tools that would be appropriate for use with the present invention.

The kit can also include a container for storing the other components of the kit. The container can be, for example, a bag, box, envelope, or any other container that would be suitable for use in the present invention. Preferably, the container is large enough to accommodate each component and/or any applicators that may be necessary for a pharmaceutical composition of the present invention. However, in some cases, it may be desirable to have a smaller container which can be hidden in a patient's pocketbook, briefcase, or pocket.

The present invention is also directed to a method of delivery of the applicators or pharmaceutical compositions of the present invention to a female in need thereof, the method comprising (a) registering in a computer readable medium the identity of a physician permitted to prescribe the applicator or composition; (b) providing the female with counseling information concerning the risks attendant to the applicator or composition; (c) obtaining informed consent from the female to receive the applicator or composition despite the attendant risks; (d) registering the female in a computer readable medium after obtaining their informed consent; and (e) permitting the female access to the applicator or composition.

The drug delivery methods of the present invention involve, inter alia, registering in a computer readable storage medium physicians who are qualified to prescribe the applicators or pharmaceutical compositions of the present invention. Once registered in the computer readable storage medium, the physician can be eligible to prescribe the applicators or pharmaceutical compositions to a female in need thereof. Generally speaking, in order to become registered in the computer readable storage medium, the physician may be required to comply with various aspects of, for example, providing patient education and counseling. The registration of the physician in the computer readable storage medium can be achieved by providing the physician, for example, by mail, facsimile transmission, or on-line transmission, with a registration card or form, preferably together with educational materials concerning the applicators or pharmaceutical compositions of the present invention. The physician can complete the registration card or form by providing information requested therein, and the registration card or form can be returned to the manufacturer or distributor of the applicators or pharmaceutical compositions of the present invention, or other authorized recipient of the registration materials, for example, by mail, facsimile transmission or on-line transmission. The physician's information in the registration card or form is then entered into the computer readable storage medium. Suitable computer readable storage media which can be employed for registration of the physicians (as well as patients, as discussed below) will be apparent to one of ordinary skill in the art, once in possession of the teaching of the present application.

In the course of examination of a patient, including a patient suffering from a menopausal condition, the physician may determine that the patient's condition can be improved by the administration of the applicators or pharmaceutical compositions of the present invention. Prior to prescribing the applicators or pharmaceutical compositions of the present invention, the physician can counsel the patient, for example, on the various risks and benefits associated with the applicators or pharmaceutical compositions. The patient can be provided full disclosure of all the known and suspected risks associated with the applicator or pharmaceutical composition. Such counseling can be provided verbally, as well as in written form. In some embodiments, the physician can provide the patient with literature materials on the applicator or pharmaceutical composition, such as product information, educational materials, and the like.

In addition to receiving counseling on the risks attendant to the applicators or pharmaceutical compositions of the present invention, the methods of the invention further require the patient to fill out an informed consent form which is signed by the patient. Upon the completion of the informed consent form, the patient can be registered in a computer readable storage medium. The computer readable storage medium in which the patient is registered can be the same as, or different from, the computer readable storage medium in which the physician is registered.

The registration into one or more computer readable storage media of the physician and patient, according to the methods describe herein, provides a means to monitor and authorize access to the applicators or pharmaceutical compositions of the present invention. Thus, the computer readable storage medium can serve to deny access to patients who fail to abide by the methods of the present invention. In some embodiments, access to the applicators or pharmaceutical compositions of the invention is in the form of a prescription, wherein the prescribing physician is registered in a computer readable storage medium, has provided counseling to the patient concerning the attendant risks of the applicators or pharmaceutical compositions, and has obtained informed consent from the patient, prior to prescribing the applicators or pharmaceutical compositions to the patient in need thereof.

The present invention is also directed to methods of educating consumers about the use of an applicator or pharmaceutical composition of the invention, the method comprising distributing the applicator or pharmaceutical composition with consumer information at a point of sale. In some embodiments, the distribution will occur at a point of sale having a pharmacist or healthcare provider.

As used herein, the term "consumer information" can include, but is not limited to, an English language text, non-English language text, visual image, chart, telephone recording, website, and access to a live customer service representative. In some embodiments of the present invention, consumer information will provide directions for use of the applicator or pharmaceutical composition of the present invention, appropriate age use, indication, contraindications, appropriate dosing, warnings, telephone number of website address. In some embodiments, the method further comprises providing professional information to relevant persons in a position to answer consumer questions regarding the applicator or pharmaceutical composition.

As used herein, the term "professional information" includes, but is not limited to, information concerning the applicator or pharmaceutical composition of the present invention designed to enable a healthcare professional to answer customer questions regarding the applicator or pharmaceutical composition.

A "relevant person," as used herein, includes, for example, a physician, physician assistant, nurse practitioner, pharmacist, and customer service representative.

All of the various embodiments or options described herein can be combined in any and all variations.

The following examples are further illustrative of the present invention, but are not to be construed to limit the scope of the present invention.

EXAMPLE 1

Aqueous-based, glycerin-based, and lipid-based monophasic pharmaceutical formulations were prepared as described in Table 3. The conjugated estrogens present in the formulations described in Table 3 contain a mixture of 9 synthetic conjugated estrogens (Diosynth, Inc., Chicago, Ill.), consisting of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, and sodium 17β-dihydroequilenin sulfate.

TABLE 3

Formulation Compositions for Conjugated Estrogens 1.25 mg/500 mg

| | | mg/500 mg | | | |
|---|---|---|---|---|---|
| | | Aqueous-based | | | Glycerin-based |
| # | Ingredients | HPMC | Carbopol ® | | Carbopol ® |
| 1 | Conjugated Estrogens DE (565 mg/g) | 2.251* | 2.212 | 2.212 | 2.251* | 2.212 |
| 2 | Carbomer 934P, NF (Carbopol ®) | — | 2 | 3.75 | 5 | — |
| 3 | Carbomer 974P, NF (Carbopol ®) | — | — | — | — | 3.75 |
| 4 | Hypromellose 2208, USP (Methocel ® K15M PR) | 15 | — | — | — | — |
| 5 | Methyl Paraben, NF | 0.4 | 0.4 | 0.4 | 0.4 | 0.4 |
| 6 | Propyl Paraben, NF | 0.1 | 0.1 | 0.1 | 0.1 | 0.1 |
| 7 | Benzyl Alcohol, NF | — | — | — | — | — |
| 8 | t-Butyl Hydroquinone | 0.1 | 0.1 | 0.1 | 0.1 | 0.1 |
| 9 | Butylated Hydroxytoluene (Food Grade, Tenox BHT) | 0.25 | — | — | — | — |
| 10 | Butylated Hydroxyanisole (Food Grade, Tenox BHA) | 0.625 | — | — | — | — |
| 11 | Vitamin E, USP (dl-alpha Tocopheryl Acetate) | 0.25 | — | — | — | — |
| 12 | Edetate Disodium Dihydrate, USP | 0.25 | 0.25 | 0.25 | 0.25 | 0.25 |
| 13 | Polysorbate 80, NF | 0.5 | 0.5 | 0.5 | 0.5 | 0.5 |
| 14 | Dehydrated Alcohol, USP (Ethyl Alcohol 200 proof) | 25 | 25 | 25 | 25 | 25 |
| 15 | Sodium Hydroxide, NF | — | 0.675 | 1.17 | 1.62 | 1.125 |
| 16 | Purified Water, USP | 405.3 | 417 | 405.3 | 432.5 | 5.1 |
| 17 | Glycerin (Anhydrous) | 50 | 50 | 61.2 | 32.3 | 461.5 |
| 18 | Gelucire ® 44/14 | — | — | — | — | — |
| 19 | Peanut Oil, NF (Refined) | — | — | — | — | — |
| 20 | Dibasic Sodium Phosphate | — | 0.75 | — | — | — |
| 21 | Hydrochloric Acid (5N) to adjust the pH | — | 3.5 | — | — | — |
| | Total Weight (mg) | 500 | 502.5 | 500 | 500 | 500 |
| | Viscosity | 817 | 8.3 | 700 | 1760 | 1700 |
| | Stability Data, % Label Claim (Initial) | | | | | |
| | Sum of Estrone + Equilin + 17α-Dihydroequilin | 95.9 | 88.6 | 87.4 | 101.3 | 96.6 |
| | Ratio of Equilin/Estrone | 0.44 | 0.43 | 0.43 | 0.43 | 0.43 |
| | 17α-Dihydroequilenin | DBNQ | 0.1 | ND | ND | ND |
| | Equilenin | 0.3 | 0.5 | 0.4 | 0.4 | 0.3 |
| | Stability Data, % Label Claim (60° C./1 week) | | | | | |
| | Sum of Estrone + Equilin + 17α-Dihydroequilin | 97.3 | 88.0 | 102.4 | 99.7 | 95.1 |
| | Ratio of Equilin/Estrone | 0.43 | 0.43 | 0.42 | 0.43 | 0.43 |
| | 17α-Dihydroequilenin | 1.1 | 0.4 | 0.9 | 0.3 | 0.4 |
| | Equilenin | 0.4 | 0.5 | 0.5 | 0.4 | 0.4 |

| | | mg/500 mg | | |
|---|---|---|---|---|
| | | Glycerin-based | | Lipid-based |
| # | Ingredients | Carbopol ® | Glycerin | Gelucire ® |
| 1 | Conjugated Estrogens DE (565 mg/g) | 2.251* | 2.251* | 2.251* |
| 2 | Carbomer 934P, NF (Carbopol ®) | — | — | — |
| 3 | Carbomer 974P, NF (Carbopol ®) | 3.75 | — | — |
| 4 | Hypromellose 2208, USP (Methocel ® K15M PR) | — | — | — |
| 5 | Methyl Paraben, NF | 0.4 | 0.4 | 0.4 |
| 6 | Propyl Paraben, NF | 0.1 | 0.1 | 0.1 |
| 7 | Benzyl Alcohol, NF | — | — | 5 |
| 8 | t-Butyl Hydroquinone | — | 0.1 | — |
| 9 | Butylated Hydroxytoluene (Food Grade, Tenox BHT) | 0.25 | 0.25 | 0.25 |
| 10 | Butylated Hydroxyanisole (Food Grade, Tenox BHA) | 0.625 | 0.625 | 0.625 |
| 11 | Vitamin E, USP (dl-alpha Tocopheryl Acetate) | 0.25 | 0.25 | 0.25 |
| 12 | Edetate Disodium Dihydrate, USP | 0.25 | 0.25 | 0.25 |
| 13 | Polysorbate 80, NF | 0.5 | 0.5 | 0.5 |
| 14 | Dehydrated Alcohol, USP (Ethyl Alcohol 200 proof) | 25 | 25 | 25 |
| 15 | Sodium Hydroxide, NF | 0.9 | — | — |
| 16 | Purified Water, USP | 4.1 | — | — |

TABLE 3-continued

Formulation Compositions for Conjugated Estrogens 1.25 mg/500 mg

| | | | | |
|---|---|---|---|---|
| 17 | Glycerin (Anhydrous) | 461.6 | 470.3 | 27.9 |
| 18 | Gelucire ® 44/14 | — | — | 425 |
| 19 | Peanut Oil, NF (Refined) | — | — | 12.5 |
| 20 | Dibasic Sodium Phosphate | — | — | — |
| 21 | Hydrochloric Acid (5N) to adjust the pH | — | — | — |
| | Total Weight (mg) | 500 | 500 | 500 |
| | Viscosity | 1011 | 6.0 | 22,200 |
| | Stability Data, % Label Claim (Initial) | | | |
| | Sum of Estrone + Equilin + 17α-Dihydroequilin | 107.0 | 98.5 | 94.1 |
| | Ratio of Equilin/Estrone | 0.44 | 0.43 | 0.43 |
| | 17α-Dihydroequilenin | DBNQ | ND | DBNQ |
| | Equilenin | 0.4 | 0.3 | 0.2 |
| | Stability Data, % Label Claim (60° C./1 week) | | | |
| | Sum of Estrone + Equilin + 17α-Dihydroequilin | 106.5 | 93.8 | 85.8 |
| | Ratio of Equilin/Estrone | 0.43 | 0.43 | 0.43 |
| | 17α-Dihydroequilenin | 0.1 | 0.3 | 0.2 |
| | Equilenin | 0.4 | 0.3 | 0.5 |

*Calculation based upon 98.3% assay. Theoretical amount = 2.212 mg. DBNQ: Detected but not quantitated. ND: Not Detected.

EXAMPLE 2

Pharmaceutical semi-solid, monophasic formulations of conjugated estrogens were prepared as described in Table 4. Two preparations of conjugated estrogens were used: (a) Conjugated Estrogens, USP (Type DE 565 mg/g), a combination of nine synthetic conjugated estrogens (Diosynth, Inc., Chicago, Ill.) consisting of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, and sodium 17β-dihydroequilenin sulfate; and (b) Conjugated Estrogens (37.5 mg/g) a combination of 10 synthetic conjugated estrogens (Organics/LaGrange, Chicago, Ill.) consisting of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate.

The Gelucire®-based formulation prepared with Conjugated Estrogens, USP (Type DE 565 mg/g) contained 85% Gelucire®, while the Gelucire®-based formulation prepared with Conjugated Estrogens (37.5 mg/g) contained 50% Gelucire®. Additionally, differing viscosities between the formulations produced from Conjugated Estrogens (37.5 mg/g) and Conjugated Estrogens (37.5 mg/g) were also attributable to differences in inactive ingredients present in the conjugated estrogens supplied by the manufacturers.

TABLE 4

Conjugated Estrogens Semi-Solid Formulations (1.25 mg/500 mg)

| | | Aqueous-based | | Glycerin-based | | Gelucire ®-based | |
|---|---|---|---|---|---|---|---|
| # | Ingredients | Conjugated Estrogens, USP (Type DE 565 mg/g) | Conjugated Estrogens (37.5 mg/g) | Conjugated Estrogens, USP (Type DE 565 mg/g) | Conjugated Estrogens (37.5 mg/g) | Conjugated Estrogens, USP (Type DE 565 mg/g) | Conjugated Estrogens (37.5 mg/g) |
| 1 | Carbomer 934P, NF (Carbopol ®) | X | X | — | — | — | — |
| 2 | Carbomer 974P, NF (Carbopol ®) | — | — | X | X | — | — |
| 3 | Gelucire ® 44/14 | — | — | — | — | X | X |
| 4 | Preservatives | X | X | X | X | X | X |
| 5 | Stabilizers | X | X | X | X | X | X |
| 6 | Permeation Enhancer | X | X | X | X | X | X |
| 7 | Alkalizing Agent | X | X | X | X | — | — |
| 8 | Ethanol | X | X | X | X | X | X |
| 9 | Purified Water, USP/Glycerin | X | X | X | X | X | X |
| | Total Weight (mg) | 500 | 500 | 500 | 500 | 500 | 500 |
| | Viscosity (Poise) | 1760 | 248 | 1011 | 93 | 22,200 | 94 |

EXAMPLE 3

Stability studies of the formulations in Table 4 were performed. Each formulation was manufactured at a batch size of 1 kg using a laboratory mixer. The final product was packaged into 75-cc amber glass bottles, heat sealed, and stored at 60° C. for stability studies.

Figure 1A:
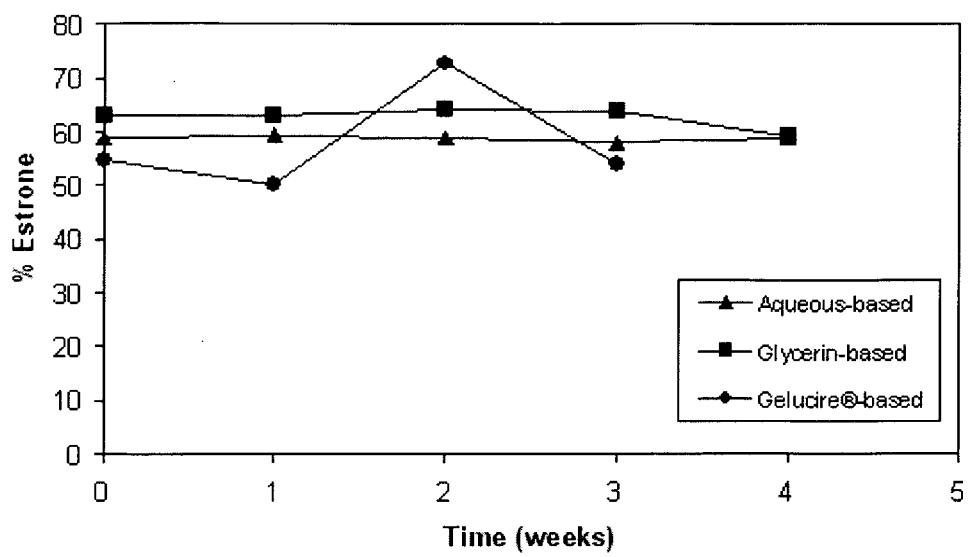
FIG. 1 shows the stability profiles of estrone (FIG. 1A) and equilin (FIG. 1B) over four weeks at 60° C. in aqueous-based (▲), glycerin-based (■), and Gelucire®-based (●) formulations containing Conjugated Estrogens, USP (Type DE, 525 mg/g).
Figure 1B:
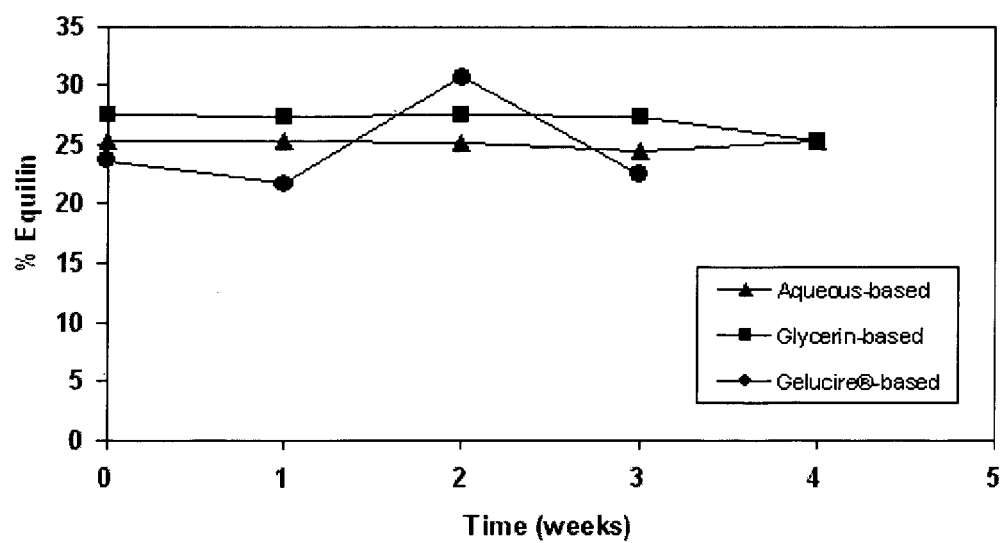
Figure 2A:
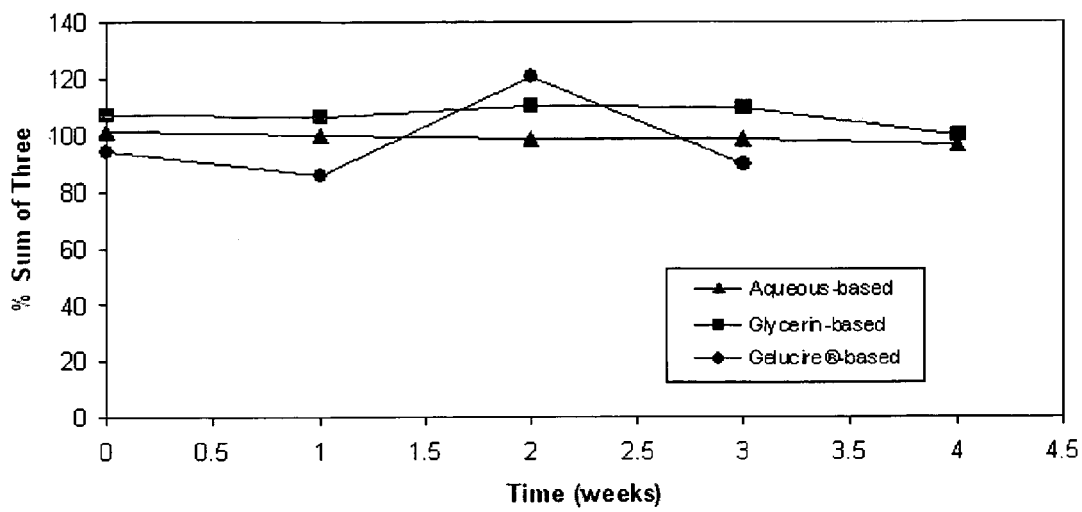
FIG. 2 shows the stability profiles of the sum of estrone+equilin+17α-dihydroequilin (FIG. 2A) and equilenin (FIG. 2B) over four weeks at 60° C. in aqueous-based (▲), glycerin-based (■), and Gelucire®-based (●) formulations containing Conjugated Estrogens, USP (Type DE, 525 mg/g).
Figure 2B:
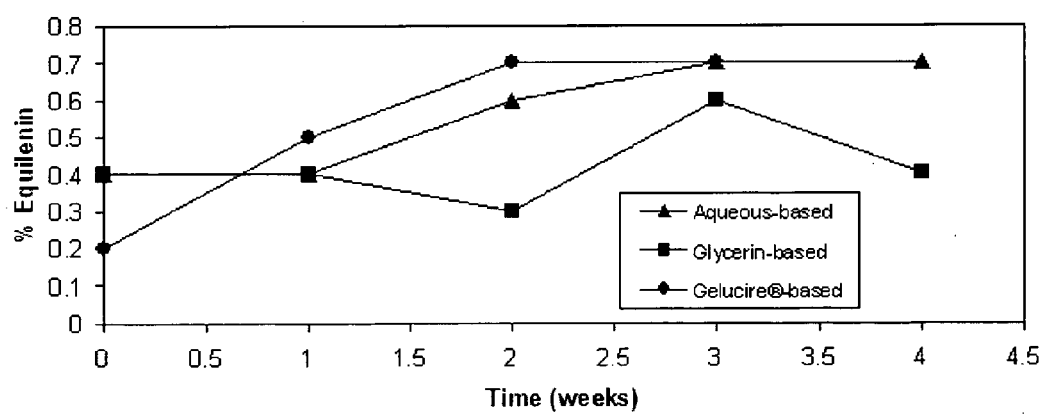
Figure 3A:
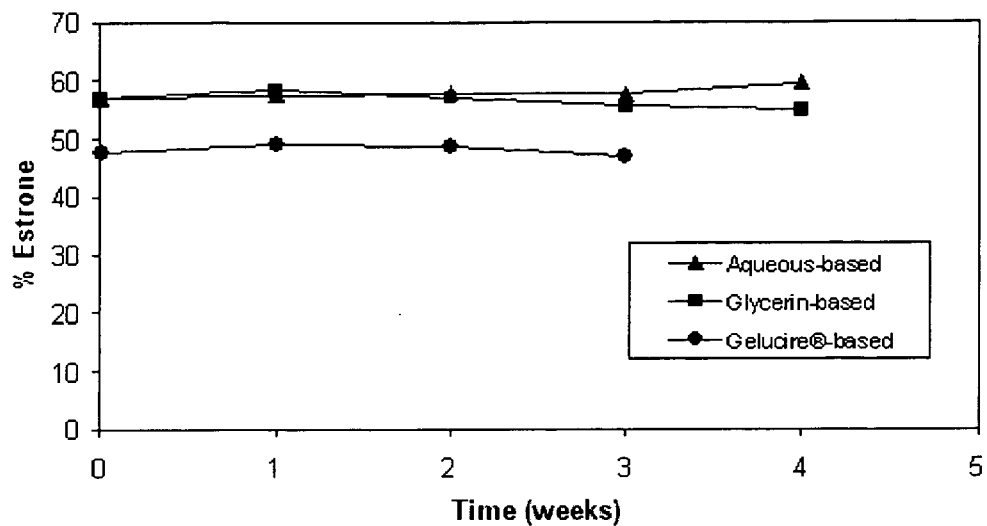
FIG. 3 shows the stability profiles of estrone (FIG. 3A) and equilin (FIG. 3B) over four weeks at 60° C. in aqueous-based (▲), glycerin-based (■), and Gelucire®-based (●) formulations containing Conjugated Estrogens (37.5 mg/g).
Figure 3B:
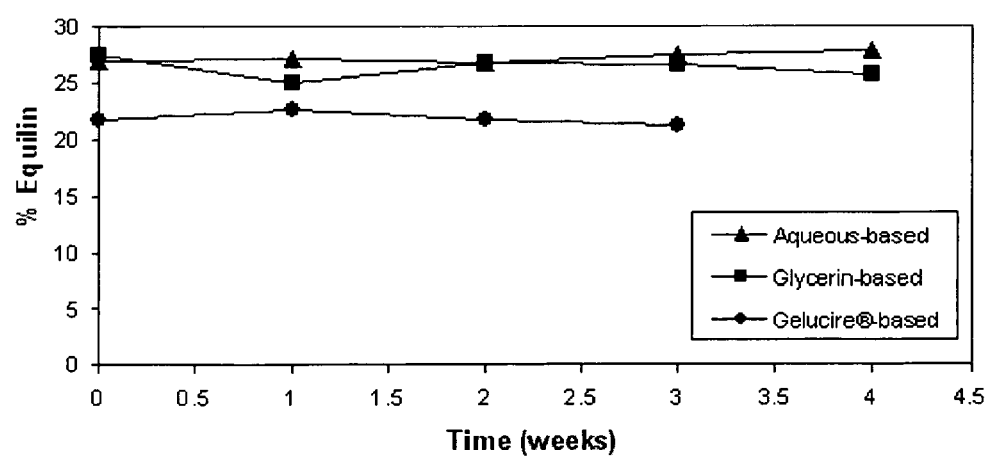
Figure 4A:
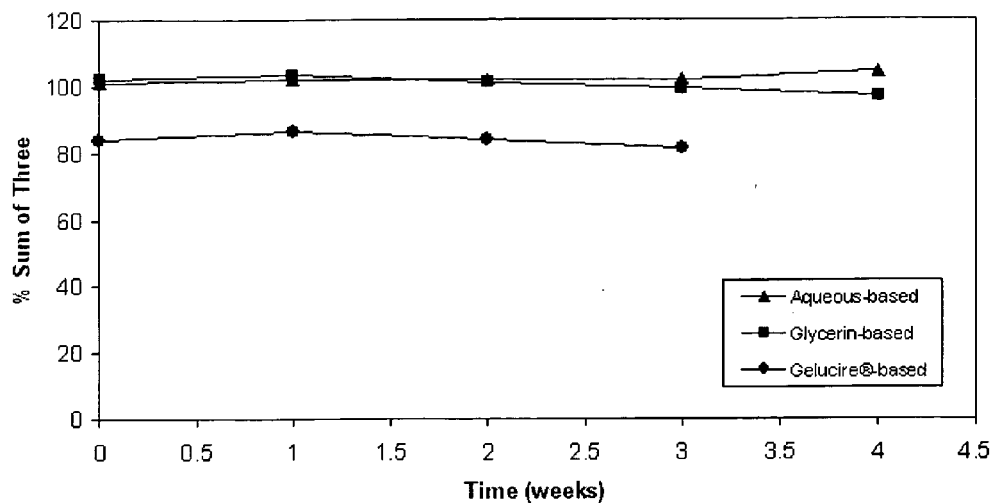
FIG. 4 shows the stability profiles of the sum of estrone+equilin+17α-dihydroequilin (FIG. 4A) and equilenin (FIG. 4B) over four weeks at 60° C. in aqueous-based (▲), glycerin-based (■), and Gelucire®-based (●) formulations containing Conjugated Estrogens (37.5 mg/g).
Figure 4B:
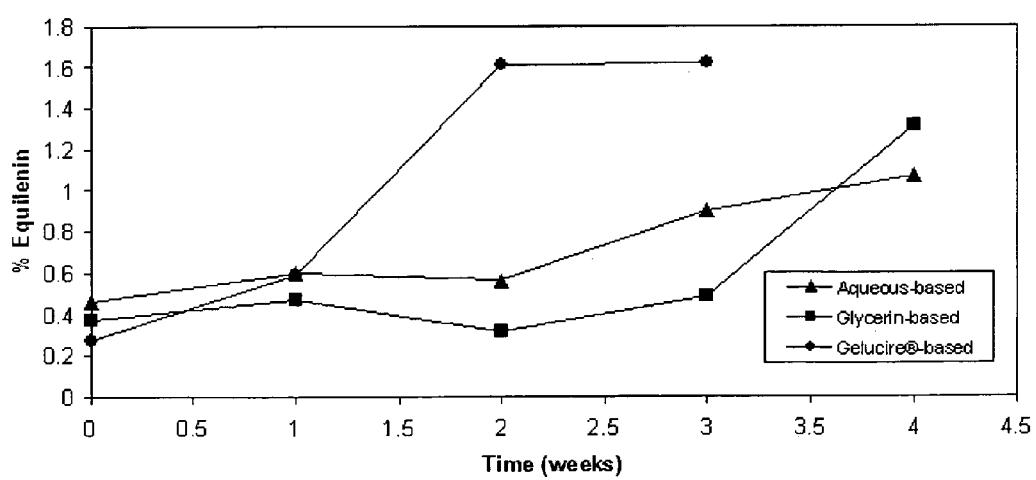

The results of the chemical stability studies as evaluated by HPLC analysis of component estrogens are shown in FIGS. 1-4. The results indicate that the ratio of equilin to estrone was substantially constant for all the formulations after 3-4 weeks at 60° C. (FIG. 1 and FIG. 3). Levels of equilenin were also measured as an indicator of degradation after 3-4 weeks at 60° C. After 3-4 weeks at 60° C., levels of equilenin were ≦0.7% in formulations prepared with Conjugated Estrogens USP (Type DE, 565 mg/g) (FIG. 2B), and ≦1.62% in formulations prepared with Conjugated Estrogens (37.5 mg/g) (FIG. 4B).

The pH of formulations prepared with Conjugated Estrogens USP (Type DE, 565 mg/g) was maintained after 3-4 weeks at 60° C. Formulations prepared with Conjugated Estrogens (37.5 mg/g) showed a slight increase in pH in the range of about 0.1 to 0.7 units after 3-4 weeks at 60° C., but remained within a pH range of 6.0 to 8.5.

EXAMPLE 4

Figure 5A:
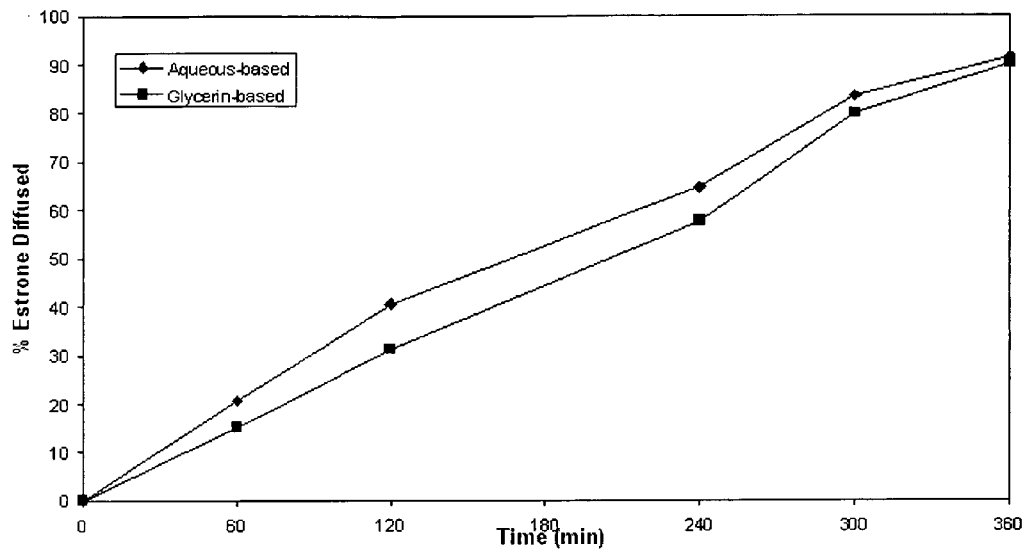
FIG. 5 shows in vitro diffusion of estrone (FIG. 5A) and equilin (FIG. 5B) against cellulose acetate membranes for aqueous-based (♦) and gylcerin-based (■) formulations containing Conjugated Estrogens (37.5 mg/g).
Figure 5B:
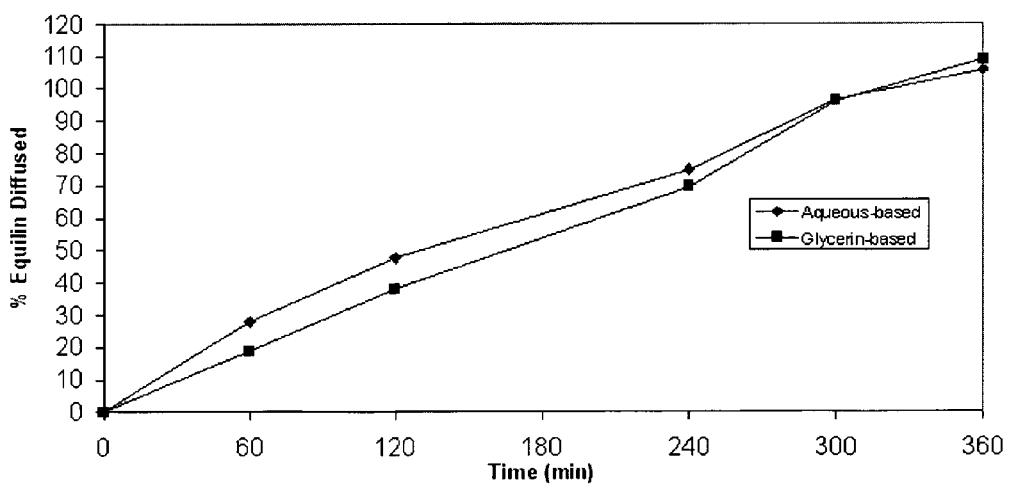

For the aqueous-based and glycerin-based formulations prepared from Conjugated Estrogens (37.5 mg/g), preliminary in vitro diffusion studies were performed measuring the diffusion of estrone (FIG. 5A) or equilin (FIG. 5B) against cellulose acetate membrane (25 mm diameter, 0.45 μm pore size) kept between the donor and receiver compartments of a Hanson's Franz Cell apparatus. The results demonstrate comparable diffusion from the aqueous-based and glycerin-based formulations.

Preliminary in vitro diffusion studies were also performed measuring the diffusion of estrone against normal human vaginal ectocervical tissue (FIGS. 6-8) to evaluate the diffusion from semi-solid, monophasic conjugated estrogens formulations in comparison with diffusion from Premarin® cream. The results demonstrate that the diffusion from the glycerin-based formulation prepared from Conjugated Estrogens (37.5 mg/g) was much higher than diffusion from Premarin® cream (FIG. 7). Diffusion from the aqueous-based and glycerin-based formulations prepared from Conjugated Estrogens USP (Type DE, 565 mg/g) was much higher than diffusion from Premarin® cream (FIG. 8).

EXAMPLE 5

Spreadability studies were also performed for the formulations described in Table 4. Spreadability studies were conducted by applying a 125 g weight load on 2 g of product placed between two petri plates. The weight was placed on the petri plate over the product and the mean diameter of spreading was monitored over 1, 5, and 15 minutes. Based upon the mean spread diameter, the spread area was calculated. See, e.g., De Paula et al., *Drug Dev Ind Pharm* 24(3): 235-241 (1998). The results for spreadability are indicated in Table 5 for spread area at 15 minutes after the 125 g load was applied.

As indicated in Table 5, all of the semi-solid, monophasic formulations displayed better spreadability as compared with Premarin® cream, and Estrace® cream, except for the Gelucire®-based formulation prepared from Conjugated Estrogens, USP (Type DE, 565 mg/g) containing 85% Gelucire®.

TABLE 5

Spreadability Data

| Product | Spread Area (cm$^2$) | % Spread as compared to estimated human vaginal surface area (87.5 cm$^2$)* |
|---|---|---|
| Water | 78.2 | 89.4 |
| Glycerin | 70.2 | 80.2 |

TABLE 5-continued

Spreadability Data

| Product | Spread Area (cm$^2$) | % Spread as compared to estimated human vaginal surface area (87.5 cm$^2$)* |
|---|---|---|
| Premarin ® cream | 57.8 | 66.1 |
| Estrace ® cream | 48.9 | 55.9 |
| Aqueous-based Conjugated Estrogens, USP (Type DE, 565 mg/g) | 70.3 | 80.3 |
| Glycerin-based Conjugated Estrogens, USP (Type DE, 565 mg/g) | 60.2 | 68.8 |
| Gelucire ® Conjugated Estrogens, USP (Type DE, 565 mg/g) | 27.5 | 31.4 |
| Aqueous-based Conjugated Estrogens (37.5 mg/g) | 69.3 | 79.2 |
| Glycerin-based Conjugated Estrogens (37.5 mg/g) | 78.8 | 90.1 |
| Gelucire ® Conjugated Estrogens (37.5 mg/g) | 84.2 | 96.2 |

*Pendergrass, P. B. et al., Gynecol Obst Invest 55(2): 110-113 (2003).

EXAMPLE 6

Aqueous-based, glycerin-based, and Gelucire®-based monophasic, semi-solid pharmaceutical formulations of conjugated estrogens were prepared as described in Table 6 and as described in FIG. 9. The synthetic conjugated estrogens in Table 6 contain a mixture of 9 estrogens (Diosynth, Inc., Chicago, Ill.): sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, and sodium 17β-dihydroequilenin sulfate. In contrast to the formulations described in Table 4, the formulations described in Table 6 do not contain ethanol.

Additional formulations containing sodium Δ8,9-dehydroestrone sulfate will be prepared.

TABLE 6

Formulation Compositions for Conjugated Estrogens (1.25 mg/500 mg)

| # | Ingredients | Aqueous-based mg/500 mg | Glycerin-based mg/500 mg | Gelucire ®-based mg/500 mg |
|---|---|---|---|---|
| 1 | Conjugated Estrogens, USP (Type DE 565 mg/g) | 2.250* | 2.250* | 2.250* |
| 2 | Carbomer 934P, NF (Carbopol ®) | 5 | — | — |
| 3 | Carbomer 974P, NF (Carbopol ®) | — | 3.75 | — |
| 4 | Gelucire ® 44/14 | — | — | 225 |
| 5 | Methyl Paraben, NF | 0.4 | 0.4 | 0.4 |
| 6 | Propyl Paraben, NF | 0.1 | 0.1 | 0.1 |
| 7 | Benzyl Alcohol, NF | 2.5 | 2.5 | — |
| 8 | Butylated Hydroxytoluene (Food Grade, Tenox BHT) | 0.25 | 0.25 | 0.25 |
| 9 | Butylated Hydroxyanisole (Food Grade, Tenox BHA) | 0.625 | 0.625 | 0.625 |
| 10 | Vitamin E, USP (dl-alpha Tocopheryl Acetate) | 0.25 | 0.25 | 0.25 |
| 11 | Edetate Disodium Dihydrate, USP | 0.25 | 0.25 | 0.25 |

TABLE 6-continued

Formulation Compositions for Conjugated Estrogens (1.25 mg/500 mg)

| # | Ingredients | Aqueous-based mg/500 mg | Glycerin-based mg/500 mg | Gelucire ®-based mg/500 mg |
|---|---|---|---|---|
| 12 | Polysorbate 80, NF | 0.5 | 0.5 | 0.5 |
| 13 | Propyleneglycol, USP | 15 | 15 | — |
| 14 | Sodium Hydroxide, NF | 1.9 | 1.0 | — |
| 15 | Purified Water, USP | 408.6 | 4.8 | 245.4 |
| 16 | Glycerin, USP | 62.35 | — | 25 |
| 17 | Glycerin (Anhydrous) | — | 468.35 | — |
|   | Total Weight | 500 mg | 500 mg | 500 mg |
|   | pH | 6.85 | 7.75 | 7.84 |
|   | Viscosity (poise) | 1529 | 603 | 1643 |

*Calculation based upon 98.3% assay. Theoretical amount = 2.212 mg

EXAMPLE 7

Stability studies of the formulations in Table 6 were performed. Formulations were packaged into 75-cc amber glass bottles, heat sealed, and stored at 60° C. for 4 weeks or were stored at 40° C. and 75% relative humidity for 1 month. The results are shown in Table 7.

The results indicate that the ratio of equilin to estrone was substantially constant for all the formulations after 4 weeks at 60° C. or after 1 month at 40° C. and 75% relative humidity. Levels of equilenin were also measured as an indicator of degradation after 4 weeks at 60° C. or after 1 month at 40° C. and 75% relative humidity. After 4 weeks at 60° C., the levels or equilenin were at 1.9%, 1.5%, or 0.8% for the aqueous-based, Gelucire®-based, and glycerin-based formulations shown in Table 7. The levels of equilenin were also substantially similar after 1 month at 40° C. and 75% relative humidity, varying by 0.3%, 0.2%, and 0% for the aqueous-based, Gelucire®-based, and glycerin-based formulations, respectively, as shown in Table 7.

EXAMPLE 8

In vitro diffusion studies were also performed measuring the diffusion of estrone against normal human vaginal ectocervical tissue (FIG. 10) to evaluate the diffusion from the semi-solid, monophasic conjugated estrogens formulations described in Table 6 in comparison with diffusion from Premarin® cream. The results demonstrate that diffusion of estrone from the aqueous-based and glycerin-based formulations was much higher than diffusion of estrone from Premarin® cream (FIG. 10).

TABLE 7

Stability Data of Conjugated Estrogens Gel Formulations at 60° C. for 4 weeks and at 40° C./75% RH for 1 Month

| Analyte | Aqueous-based | | | | | | Gelucire ®-Based | | |
|---|---|---|---|---|---|---|---|---|---|
| | Initial | 60 C. 1 wk | 60 C. 2 wks | 60 C. 3 wks | 60 C. 4 wks | 40 C./ 75% RH 1 Month | Initial | 60 C. 1 wk | 60 C. 2 wks |
| Estrone (Es) | 61.4 | 62.0 | 62.5 | 62.4 | 62.5 | 62.0 | 59.4 | 60.7 | 61.1 |
| Equilin (Eq) | 28.0 | 26.6 | 26.1 | 26.9 | 26.4 | 27.1 | 27.1 | 26.3 | 25.9 |
| 17α-DHQ | 18.5 | 17.6 | 17.1 | 17.8 | 17.1 | 18.0 | 18.0 | 17.7 | 17.4 |
| Sum of three | 107.9 | 106.2 | 105.7 | 107.1 | 106.0 | 107.1 | 104.5 | 104.7 | 104.4 |
| Ratio of Eq/Es | 0.46 | 0.43 | 0.42 | 0.43 | 0.42 | 0.44 | 0.46 | 0.43 | 0.42 |
| 17α-DHQN | ND | 0.6 | 1.1 | 0.7 | 1.6 | 0.3 | ND | 0.3 | 0.6 |
| Equilenin | 0.5 | 1.0 | 1.4 | 1.0 | 1.9 | 0.8 | 0.3 | 0.8 | 1.1 |

| Analyte | Gelucire ®-Based | | | Glycerin-based | | | | | |
|---|---|---|---|---|---|---|---|---|---|
| | 60 C. 3 wks | 60 C. 4 wks | 40 C./ 75% RH 1 Month | Initial | 60 C. 1 wk | 60 C. 2 wks | 60 C. 3 wks | 60 C. 4 wks | 40 C./ 75% RH 1 Month |
| Estrone (Es) | 59.4 | 61.1 | 60.7 | 57.2 | 57.9 | 55.0 | 59.2 | 55.0 | 57.9 |
| Equilin (Eq) | 25.0 | 26.1 | 27.1 | 26.1 | 25.6 | 24.1 | 25.9 | 26.9 | 26.6 |
| 17α-DHQ | 16.7 | 17.3 | 18.2 | 17.3 | 17.2 | 16.2 | 17.4 | 18.0 | 17.9 |
| Sum of three | 101.1 | 104.5 | 106.0 | 100.6 | 100.7 | 95.3 | 102.5 | 99.9 | 102.4 |
| Ratio of Eq/Es | 0.42 | 0.43 | 0.45 | 0.46 | 0.44 | 0.44 | 0.44 | 0.49 | 0.46 |
| 17α-DHQN | 0.7 | 1.0 | 0.6 | ND | ND | 0.2 | 0.3 | 0.3 | ND |
| Equilenin | 1.1 | 1.5 | 0.5 | 0.4 | 0.4 | 0.6 | 0.6 | 0.8 | 0.4 |

17α-DHQ: 17-αDihydroequilin; 17α-DHQN: 17-αDihydroequilenin.

EXAMPLE 9

Spreadability studies were also performed for the formulations described in Table 6 with results as indicated in Table 8.

As indicated in Table 8, all of the semi-solid, monophasic formulations displayed better spreadability as compared with Premarin® cream, and Estrace® cream.

TABLE 8

Spreadability Data

| Product | Spread Area (cm$^2$) | % Spread as compared to estimated human vaginal surface area (87.5 cm$^2$)* |
|---|---|---|
| Water | 78.2 | 89.4 |
| Glycerin | 70.2 | 80.2 |
| Premarin ® cream | 57.8 | 66.1 |
| Estrace ® cream | 48.9 | 55.9 |
| Aqueous-based Conjugated Estrogens, USP (Type DE, 565 mg/g) | 67.2 | 76.8 |
| Glycerin-based Conjugated Estrogens, USP (Type DE, 565 mg/g) | 74.2 | 84.8 |
| Gelucire ® Conjugated Estrogens, USP (Type DE, 565 mg/g) | 63.7 | 72.8 |

*Pendergrass, P. B. et al., Gynecol Obst Invest 55(2): 110-113 (2003).

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An applicator comprising a single unit-dose of a monophasic pharmaceutical composition comprising a conjugated estrogen and a hydrophilic excipient,
   wherein the composition has a viscosity greater than about 1 Poise and less than about 30,000 Poise,
   wherein the conjugated estrogen comprises a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate,
   and wherein the diffusion of estrone or equilin from the composition across human vaginal tissue is from about 30% to about 90% at 24 hours.

2. The applicator of claim 1, wherein the conjugated estrogen consists of a combination of sodium estrone sulfate, sodium equilin sulfate, sodium 17αa-dihydroequilin sulfate, sodium 17β-dihydroequilin sulfate, sodium 17αa-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate.

3. The applicator of claim 1, wherein the hydrophilic excipient is selected from the group consisting of water, glycerin, propylene glycol, polyethylene glycol, polyol, alcohol, and combinations thereof.

4. The applicator of claim 1, wherein the composition comprises a pharmaceutically acceptable excipient selected from the group consisting of an alkaline agent, a stabilizer, an adhesion agent, a solvent, a surfactant, a humectant, a buffering agent, and combinations thereof.

5. The applicator of claim 4, wherein the alkaline agent is an inorganic base selected from the group consisting of hydroxides and oxides of alkali metals, alkaline earth metals, and combinations thereof.

6. The applicator of claim 4, wherein the alkaline agent is an organic base comprising an amine.

7. The applicator of claim 4, wherein the stabilizer is selected from the group consisting of methyl paraben, propyl paraben, t-butyl hydroquinone, butylated hydroxyanisole, butylated hydroxytoluene, ascorbic acid and its esters, vitamin E and its esters, sodium bisulfite, sodium metabisulfite, 3-dehydroshikimic acid, tocopherols and their esters, alkyl gallates, chelating agents, EDTA, edetate disodium, citric acid, benzyl alcohol, and combinations thereof.

8. The applicator of claim 4, wherein the adhesion agent is selected from the group consisting of hydrogenated vegetable oil, polyethylene glycol, cetyl alcohol, cetyl esters wax, microcrystalline wax, paraffin, ethyl alcohol, stearyl alcohol, lauryl alcohol, myristyl alcohol, cetostearyl alcohol, white wax, yellow wax, beeswax, candelilla wax, cotton wax, carnauba wax, bayberry wax, ice-bran wax, carbomer, hydroxypropylmethylcellulose, hypromellose, starch, methylcellulose, microcrystalline cellulose, and combinations thereof.

9. The applicator of claim 4, wherein the solvent is selected from the group consisting of water, glycerin, dehydrated alcohol, glyceryl esters of fatty acids, lauryl macrogolglycerides, polyoxyethylene alkyl ethers, and combinations thereof.

10. The applicator of claim 4, wherein the surfactant is selected from the group consisting of sodium lauryl sulfate, polysorbate 80, poloxamer, lauryl macrogolglycerides, polyoxyethylene alkyl ethers, and combinations thereof.

11. The applicator of claim 4, wherein the humectant is selected from the group consisting of polyethylene glycol, propylene glycol, glycerin, polyol, polyol derivatives, and combinations thereof.

12. The applicator of claim 4, wherein the buffering agent is selected from the group consisting of Tris buffers, Tris EDTA, Tris acetate, Tris phosphate, Tris glycine, phosphate buffers, sodium phosphate, sodium phosphate dibasic, potassium phosphate, bicarbonate buffers, acetate buffers, ammonium buffers, citrate buffers, organic acid buffers, zwitterionic buffers, and derivatives and combinations thereof.

13. The applicator of claim 1, wherein the composition is substantially free of ethanol.

14. The applicator of claim 1, wherein the applicator is a vaginal applicator.

15. The applicator of claim 1, wherein the composition has a viscosity greater than about 50 Poise and less than about 2,500 Poise.

16. The applicator of claim 1, wherein the composition has a viscosity greater than about 90 Poise and less than about 2,000 Poise.

17. The applicator of claim 1, wherein the diffusion of estrone or equilin from the composition across human vaginal tissue is from about 40% to about 90% at 24 hours.

18. A monophasic pharmaceutical composition comprising:
a conjugated estrogen and a hydrophilic excipient,
wherein the composition has a viscosity greater than about 1 Poise and less than about 30,000 Poise,
wherein the conjugated estrogen comprises a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate,
and wherein the diffusion of estrone or equilin from the composition across human vaginal tissue is from about 30% to about 90% at 24 hours.

19. A monophasic pharmaceutical composition comprising:
a conjugated estrogen and a hydrophilic excipient,
wherein the composition has a viscosity greater than about 50 Poise and less than about 2,500 Poise,
wherein the conjugated estrogen comprises a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate,
and wherein the diffusion of estrone or equilin from the composition across human vaginal tissue is from about 40% to about 90% at 24 hours.

20. A monophasic pharmaceutical composition comprising:
a conjugated estrogen and a hydrophilic excipient,
wherein the composition has a viscosity greater than about 90 Poise and less than about 2,000 Poise,
wherein the conjugated estrogen comprises a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17αa-dihydroequilenin sulfate, sodium 17β-dihydroequilenin sulfate, and sodium Δ8,9-dehydroestrone sulfate,
and wherein the diffusion of estrone or equilin from the composition across human vaginal tissue is from about 50% to about 90% at 24 hours.

21. A kit comprising one or more applicators, wherein each applicator comprises a single unit-dose of a monophasic pharmaceutical composition comprising a conjugated estrogen and a hydrophilic excipient,
wherein the composition has a viscosity greater than about 1 Poise and less than about 30,000 Poise,
wherein the conjugated estrogen comprises a combination of sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate,
and wherein the diffusion of estrone or equilin from the composition across human vaginal tissue is from about 30% to about 90% at 24 hours.

22. The kit of claim 21, wherein the applicator is a vaginal applicator.

23. The kit of claim 21, further comprising printed instructions for use of the kit.

24. The applicator of claim 1, wherein the sodium estrone sulfate, sodium equilin sulfate, sodium 17α-dihydroequilin sulfate, sodium 17β-dihydroequilin sulfate, sodium 17α-estradiol sulfate, sodium 17β-estradiol sulfate, sodium equilenin sulfate, sodium 17α-dihydroequilenin sulfate, sodium 17β-dihydroequilenin sulfate, and sodium Δ8,9-dehydroestrone sulfate are synthetic conjugated estrogens.

25. The applicator of claim 1, wherein the single unit-dose is an amount of about 50 mg to about 7.5 g of the composition.

26. The applicator of claim 1, wherein the single unit-dose is an amount of about 100 mg to about 1 g of the composition.

27. The applicator of claim 1, wherein the single unit-dose is an amount of about 50 mg to about 500 mg of the composition.

28. The applicator of claim 1, wherein the composition comprises about 0.1 mg to about 15 mg of the conjugated estrogen.

29. The applicator of claim 1, wherein the conjugated estrogen is about 0.02% to about 5% of the total weight of the composition.

30. The applicator of claim 1, wherein the diffusion of estrone or equilin from the composition across human vaginal tissue is from about 50% to about 90% at 24 hours.

31. The applicator of claim 1, wherein the composition further comprises carbomer.

32. The applicator of claim 31, wherein the hydrophilic excipient comprises water and glycerin.

* * * * *